US012557982B2

(12) United States Patent
Hirokawa et al.

(10) Patent No.: US 12,557,982 B2
(45) Date of Patent: Feb. 24, 2026

(54) IMAGE PROCESSING METHOD, IMAGE PROCESSING DEVICE, AND PROGRAM

(71) Applicant: NIKON CORPORATION, Tokyo (JP)

(72) Inventors: Mariko Hirokawa, Yokohama (JP); Yasushi Tanabe, Fujisawa (JP)

(73) Assignee: NIKON CORPORATION, Tokyo (JP)

( * ) Notice: Subject to any disclaimer, the term of this patent is extended or adjusted under 35 U.S.C. 154(b) by 960 days.

(21) Appl. No.: 17/770,878

(22) PCT Filed: Oct. 25, 2019

(86) PCT No.: PCT/JP2019/041982
§ 371 (c)(1),
(2) Date: Aug. 30, 2022

(87) PCT Pub. No.: WO2021/079504
PCT Pub. Date: Apr. 29, 2021

(65) Prior Publication Data
US 2023/0000337 A1     Jan. 5, 2023

(51) Int. Cl.
*A61B 3/00*          (2006.01)
*A61B 3/10*          (2006.01)
*A61B 3/15*          (2006.01)

(52) U.S. Cl.
CPC ............ *A61B 3/0025* (2013.01); *A61B 3/102* (2013.01); *A61B 3/152* (2013.01)

(58) Field of Classification Search
CPC ....... A61B 3/0025; A61B 3/102; A61B 3/152; A61B 3/12

USPC .......................................................... 351/205
See application file for complete search history.

(56) References Cited

U.S. PATENT DOCUMENTS

2007/0291277 A1* 12/2007 Everett .............. G01B 9/02077
                                                    356/497
2012/0120368 A1*  5/2012 Fujimora ............... A61B 3/102
                                                    382/131
2017/0105618 A1*  4/2017 Schmoll .............. A61B 3/0025
2020/0258295 A1   8/2020 Hirokawa

FOREIGN PATENT DOCUMENTS

JP        2006061196 A  *  3/2006
WO     WO-2019074077 A1 *  4/2019  ........... A61B 8/4416

OTHER PUBLICATIONS

Office Action issued in corresponding Japanese Patent Application No. 2021-553267 dated Jun. 6, 2023 (9 pages).

* cited by examiner

*Primary Examiner* — Mohammed A Hasan
(74) *Attorney, Agent, or Firm* — Foley & Lardner LLP

(57) ABSTRACT

Image processing performed by a processor and including acquiring a two-dimensional fundus image, acquiring a second point on an eyeball model corresponding to at least one first point of the two-dimensional fundus image, and creating data to represent a process to move the first point to the second point.

15 Claims, 26 Drawing Sheets

110
OPHTHALMIC DEVICE

130

140

120
EYE AXIAL LENGTH MEASUREMENT DEVICE

150 f1 fd fh fm fr

TIME

IMAGE PROCESSING METHOD, IMAGE PROCESSING DEVICE, AND PROGRAM

The present technology disclosed herein relates to an image processing method, an image processing device, and a program.

BACKGROUND ART

A panorama fundus image combining device and method are disclosed in United States Patent Application Publication No. 2009/0136100, and there is a desire for an appropriate image display method for analyzing and examining a fundus.

SUMMARY OF INVENTION

A first aspect of technology disclosed herein is image processing performed by a processor and including acquiring a two-dimensional fundus image, acquiring a second point on an eyeball model corresponding to at least one first point of the two-dimensional fundus image, and creating data to represent a process to move the first point to the second point.

An image processing device of a second aspect of technology disclosed herein including a memory, and a processor coupled to the memory. The processor is configured to acquire a two-dimensional fundus image, acquire a second point on an eyeball model corresponding to at least one first point of the two-dimensional fundus image, and create data to represent a process to move the first point to the second point.

A program of a third aspect of technology disclosed herein causes a computer to execute processing including acquiring a two-dimensional fundus image, acquiring a second point on an eyeball model corresponding to at least one first point of the two-dimensional fundus image, and creating data to represent a process to move the first point to the second point.

BRIEF DESCRIPTION OF DRAWINGS

FIG. 1 is a block diagram of an ophthalmic system 100.

FIG. 12 is a diagram illustrating a first display pattern of a display screen 400A.

FIG. 20 is diagram for explaining generation of a montage image GM.

FIG. 22 is a diagram illustrating a second display format of the display screen 400B.

DESCRIPTION OF EMBODIMENTS

First Exemplary Embodiment

Figure 2:
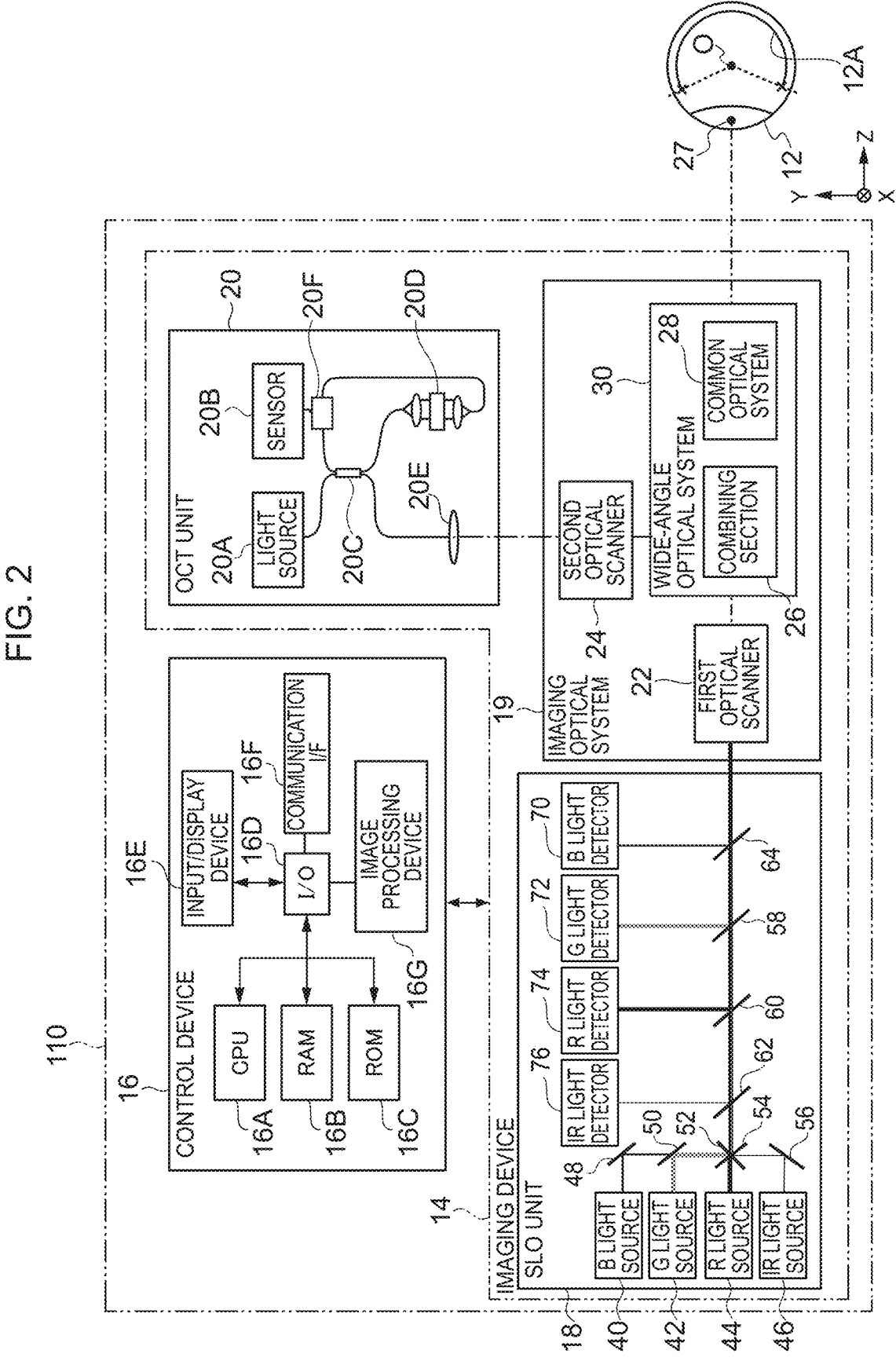
FIG. 2 is a schematic configuration diagram illustrating an overall configuration of an ophthalmic device 110.

Detailed explanation follows regarding a first exemplary embodiment of technology disclosed herein, with reference to the drawings.

Figure 1:
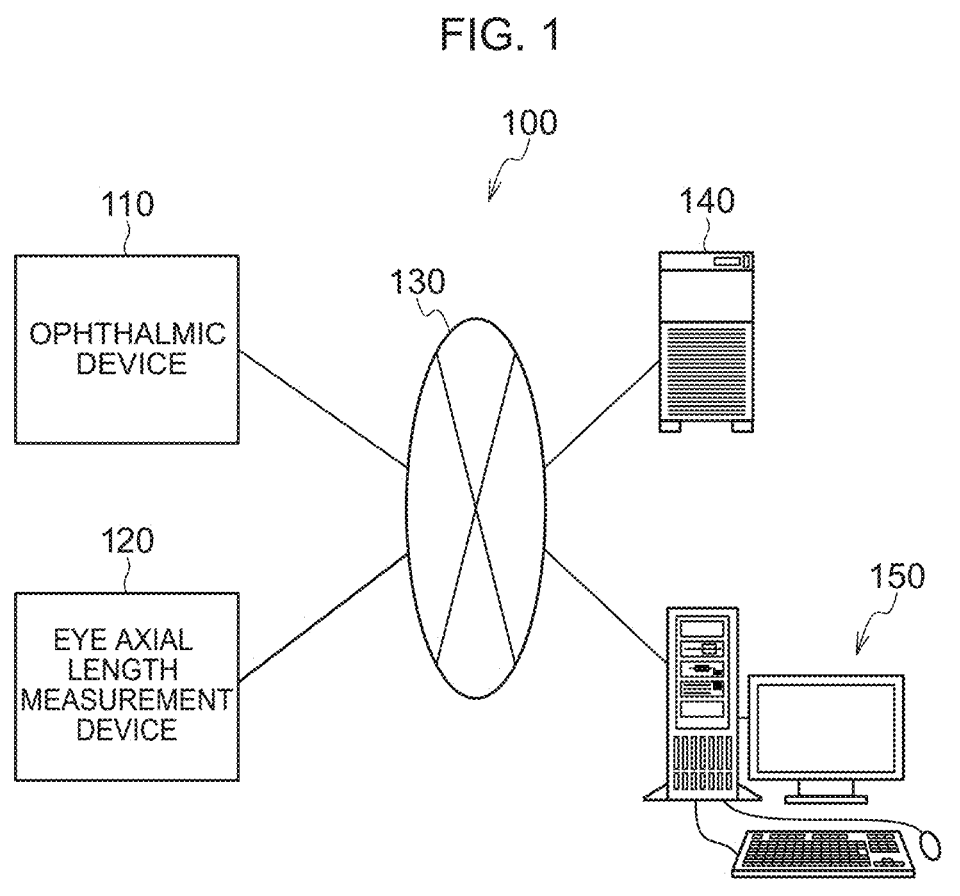

Explanation follows regarding a configuration of an ophthalmic system 100, with reference to FIG. 1. As illustrated in FIG. 1, the ophthalmic system 100 includes an ophthalmic device 110, an eye axial length measurement device 120, a management server device (referred to hereafter as "server") 140, and an image display device (referred to hereafter as "viewer") 150. The ophthalmic device 110 acquires an image of the fundus. The eye axial length measurement device 120 measures the axial length of the eye of a patient. The server 140 stores fundus images that were obtained by imaging the fundus of patients using the ophthalmic device 110 in association with patient IDs. The viewer 150 displays medical information such as fundus images acquired from the server 140.

The ophthalmic device 110, the. eye axial length measurement device 120, the server 140, and the viewer 150 are connected together through a network 130.

Next, explanation follows regarding a configuration of the ophthalmic device 110, with reference to FIG. 2.

For ease of explanation, scanning laser ophthalmoscope is abbreviated to SLO. Optical coherence tomography is also abbreviated to OCT.

With the ophthalmic device 110 installed on a horizontal plane and a horizontal direction taken as an X direction, a direction perpendicular to the horizontal plane is denoted a Y direction, and a direction connecting the center of the pupil at the anterior eye portion of the examined eye 12 and the center of the eyeball is denoted a Z direction. The X direction, the Y direction, and the Z direction are thus mutually perpendicular directions.

The ophthalmic device 110 includes an imaging device 14 and a control device 16. The imaging device 14 is provided with an SLO unit 18, an OCT unit 20, and an imaging optical system 19, and acquires a fundus image of the fundus of the examined eye 12. Two-dimensional fundus images that have been acquired by the SLO unit 18 are referred to hereafter as SLO images. Tomographic images, face-on images (en-face images) and the like of the retina created based on OCT data acquired by the OCT unit 20 are referred to hereafter as OCT images.

The control device 16 includes a computer provided with a Central Processing Unit (CPU) 16A, Random Access Memory (RAM) 16B, Read-Only Memory (ROM) 16C, and an input/output (I/O) port 16D.

The control device 16 is provided with an input/display device 16E connected to the CPU 16A through the I/O port 16D. The input/display device 16E includes a graphical user interface to display images of the examined eye 12 and to receive various instructions from a user. An example of the graphical user interface is a touch panel display.

The control device 16 is also provided with an image processing device 16G connected to the I/O port 16D. The image processing device 16G generates images of the examined eye 12 based on data acquired by the imaging device 14. The control device 16 is provided with a communication interface (I/F) 16F connected to the I/O port 16D. The ophthalmic device 110 is connected to the eye axial length measurement device 120, the server 140, and the viewer 150 through the communication interface (I/F) 16F and the network 130.

Although the control device 16 of the ophthalmic device 110 is provided with the input/display device 16E as illustrated in FIG. 2, the technology disclosed herein is not limited thereto. For example, a configuration may adopted in which the control device 16 of the ophthalmic device 110 is not provided with the input/display device 16E, and instead a separate input/display device is provided that is physically independent of the ophthalmic device 110. In such cases, the display device is provided with an image processing processor unit that operates under the control of the CPU 16A in the control device 16. Such an image processing processor unit may display SLO images and the like based on an image signal output as an instruction by the CPU 16A.

The imaging device 14 operates under the control of the CPU 16A of the control device 16. The imaging device 14 includes the SLO unit 18, the imaging optical system 19, and the OCT unit 20. The imaging optical system 19 includes a first optical scanner 22, a second optical scanner 24, and a wide-angle optical system 30.

The first optical scanner 22 scans light emitted from the SLO unit 18 two dimensionally in the X direction and the Y direction. The second optical scanner 24 scans light emitted from the OCT unit 20 two dimensionally in the X direction and the Y direction. As long as the first optical scanner 22 and the second optical scanner 24 are optical elements capable of deflecting light beams, they may be configured by any out of, for example, polygon mirrors, mirror galvanometers, or the like. A combination thereof may also be employed.

The wide-angle optical system 30 includes an objective optical system (not illustrated in FIG. 2) provided with a common optical system 28, and a combining section 26 that combines light from the SLO unit 18 with light from the OCT unit 20.

The objective optical system of the common optical system 28 may be a reflection optical system employing a concave mirror such as an elliptical mirror, a refraction optical system employing a wide-angle lens, or may be a reflection-refraction optical system employing a combination of a concave mirror and a lens. Employing a wide-angle optical system that utilizes an elliptical mirror, wide-angle lens, or the like enables imaging to be performed not only of a central portion of the fundus where the optic nerve head and macular are present, but also of the retina at a fundus peripheral portion where an equatorial portion of the eyeball and vortex veins are present.

For a system including an elliptical mirror, a configuration may be adopted that utilizes an elliptical mirror system as disclosed in International Publication (WO) Nos. 2016/103484 or 2016/103489. The disclosures of WO Nos. 2016/103484 and 2016/103489 are incorporated in their entirety by reference herein.

Observation of the fundus over a wide field of view (FOV) 12A is implemented by employing the wide-angle optical system 30. The FOV 12A refers to a range capable of being imaged by the imaging device 14. The FOV 12A may be expressed as a viewing angle. In the present exemplary embodiment the viewing angle may be defined in terms of an internal illumination angle and an external illumination angle. The external illumination angle is the angle of illumination by a light beam shone from the ophthalmic device 110 toward the examined eye 12, and is an angle of illumination defined with respect to the pupil 27. The internal illumination angle is the angle of illumination of a light beam shone onto the fundus, and is an angle of illumination defined with respect to the eyeball center O. A correspondence relationship exists between the external illumination angle and the internal illumination angle. For example, an external illumination angle of 120° is equivalent to an internal illumination angle of approximately 160°. The internal illumination angle in the present exemplary embodiment is 200°.

An angle of 200° for the internal illumination angle is an example of a "specific value" of technology disclosed herein.

Figure 7A:
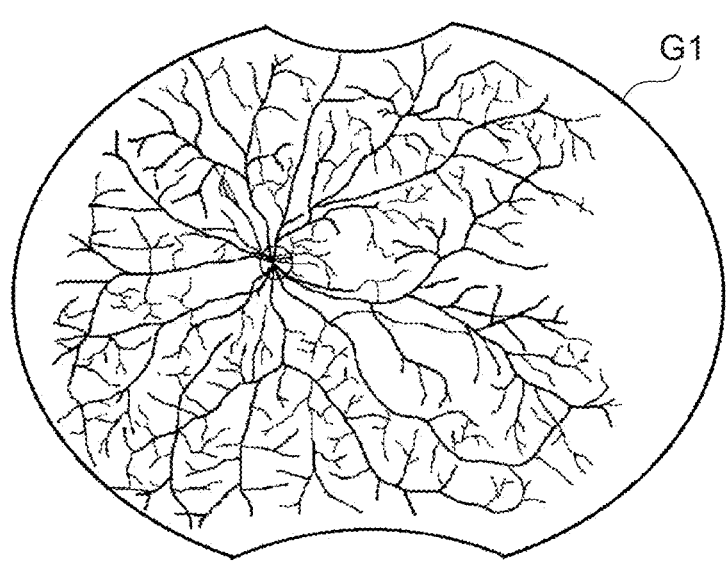
FIG. 7A is a diagram illustrating a UWF fundus image G1.

SLO fundus images obtained by imaging at an imaging angle having an internal illumination angle of 160° or greater are referred to as UWF-SLO fundus images (see FIG. 7A). UWF is an abbreviation of ultra-wide field. Obviously an SLO image that is not UWF can be acquired by imaging the fundus at an imaging angle that is an internal illumination angle of less than 160°.

The UWF-SLO fundus images imaged by the wide-angle optical system of the ophthalmic device 110 are images resulting from stereographic projection transformation of retinal images of the eyeball onto a two-dimensional flat plane. The fundus peripheral portion suffers from a greater distortion of distances and surface area under stereographic projection transformation than a fundus center portion. Thus there is an issue that as a result of the surface area and shape of structures and pathological lesions present at the fundus peripheral portion and the fundus equatorial portion, such as for example fundus structures of vortex veins and detached retina, appearing distorted, ascertaining the position of these subjects on the eyeball in relation to the periphery is difficult in the UWF-SLO fundus image, which is a two-dimensional fundus image.

Figure 7B:
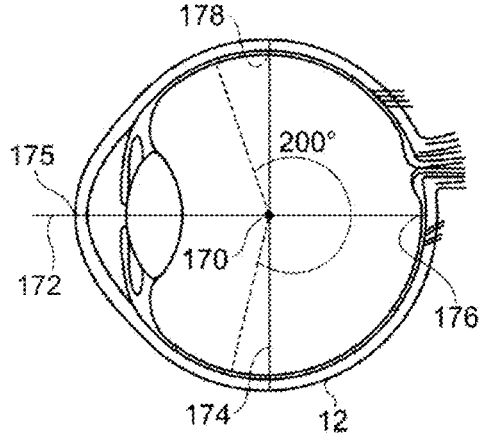
FIG. 7B is a diagram illustrating an eyeball and an imaging angle.

Explanation follows regarding a fundus equatorial portion 174, with reference to FIG. 7B. The eyeball (examined eye 12) is a spherical structure with a diameter of approximately 24 mm and an eyeball center 170. A straight line joining an anterior pole 175 to a posterior pole 176 is referred to as an ocular axis 172, a line running along an intersection between a plane orthogonal to the ocular axis 172 and the eyeball surface is referred to as a line of latitude, and the equator 174 corresponds to the line of latitude with the greatest length. Portions of the retina and the choroid coinciding with the position of the equator 174 configure an equatorial portion 178. The equatorial portion 178 corresponds to one part of a fundus peripheral portion.

An SLO system is realized by the control device 16, the SLO unit 18, and the imaging optical system 19 as illustrated in FIG. 2. The SLO system is provided with the wide-angle optical system 30, enabling fundus imaging over the wide FOV 12A.

The SLO unit 18 is provided with plural light sources such as, for example, a blue (B) light source 40, a green (G) light source 42, a red (R) light source 44, an infrared (for example near infrared) (IR) light source 46, and optical systems 48, 50, 52, 54, 56 to guide the light from the light sources 40, 42, 44, 46 onto a single optical path using reflection or transmission. The optical systems 48, 50, 56 are configured by mirrors, and the optical systems 52, 54 are configured by beam splitters. B light is reflected by the optical system 48, is transmitted through the optical system 50, and is reflected by the optical system 54. G light is reflected by the optical systems 50, 54, R light is transmitted through the optical systems 52, 54, and IR light is reflected by the optical systems 56, 52. The respective lights are thereby guided onto a single optical path.

The SLO unit 18 is configured so as to be capable of switching between the light source or the combination of light sources employed for emitting laser light of different wavelengths, such as a mode in which G light, R light and B light are emitted, a mode in which infrared light is emitted, etc. Although the example in FIG. 2 includes four light sources, i.e. the B light source 40, the G light source 42, the R light source 44, and the IR light source 46, the technology disclosed herein is not limited thereto. For example, the SLO unit 18 may, furthermore, also include a white light source, in a configuration in which light is emitted in various modes, such as a mode in which white light is emitted alone.

Light introduced to the imaging optical system 19 from the SLO unit 18 is scanned in the X direction and the Y direction by the first optical scanner 22. The scanning light passes through the wide-angle optical system 30 and the pupil 27 and is shone onto the posterior eye portion of the examined eye 12. Reflected light that has been reflected by the fundus passes through the wide-angle optical system 30 and the first optical scanner 22 and is introduced into the SLO unit 18.

The SLO unit 18 is provided with a beam splitter 64 that, from out of the light coming from the posterior eye portion (e.g. fundus) of the examined eye 12, reflects the B light therein and transmits light other than B light therein, and a beam splitter 58 that, from out of the light transmitted by the beam splitter 64, reflects the G light therein and transmits light other than G light therein. The SLO unit 18 is further provided with a beam splitter 60 that, from out of the light transmitted through the beam splitter 58, reflects R light therein and transmits light other than R light therein. The SLO unit 18 is further provided with a beam splitter 62 that reflects IR light from out of the light transmitted through the beam splitter 60.

The SLO unit 18 is provided with plural light detectors corresponding to the plural light sources. The SLO unit 18 includes a B light detector 70 for detecting B light reflected by the beam splitter 64, and a G light detector 72 for detecting G light reflected by the beam splitter 58. The SLO unit 18 includes an R light detector 74 for detecting R light reflected by the beam splitter 60 and an IR light detector 76 for detecting IR light reflected by the beam splitter 62.

Light that has passed through the wide-angle optical system 30 and the first optical scanner 22 and been introduced into the SLO unit 18 (i.e. reflected light that has been reflected by the fundus) is reflected by the beam splitter 64 and photo-detected by the B light detector 70 when B light, and is transmitted through the beam splitter 64 and reflected by the beam splitter 58 and photo-detected by the G light detector 72 when G light. When R light, the incident light is transmitted through the beam splitters 64, 58, reflected by the beam splitter 60, and photo-detected by the R light detector 74. When IR light, the incident light is transmitted through the beam splitters 64, 58, 60, reflected by the beam splitter 62, and photo-detected by the IR light detector 76. The image processing device 16G that operates under the control of the CPU 16A employs signals detected by the B light detector 70, the G light detector 72, the R light detector 74, and the IR light detector 76 to generate UWF-SLO images.

The UWF-SLO image (hereafter sometimes referred to as a UWF fundus image or an original fundus image) encompasses a UWF-SLO image (green fundus image) obtained by imaging the fundus in green, and a UWF-SLO image (red fundus image) obtained by imaging the fundus in red. The UWF-SLO image further encompasses a UWF-SLO image (blue fundus image) obtained by imaging the fundus in blue, and a UWF-SLO image (IR fundus image) obtained by imaging the fundus in IR.

The control device 16 also controls the light sources 40, 42, 44 so as to emit light at the same time. A green fundus image, a red fundus image, and a blue fundus image are obtained with mutually corresponding positions by imaging the fundus of the examined eye 12 at the same time with the B light, G light, and R light. An RGB color fundus image is obtained from the green fundus image, the red fundus image, and the blue fundus image. The control device 16 obtains a green fundus image and a red fundus image with mutually corresponding positions by controlling the light sources 42, 44 so as to emit light at the same time and by imaging the fundus of the examined eye 12 at the same time with the G light and R light. A RG color fundus image is obtained from the green fundus image and the red fundus image.

Specific examples of the UWF-SLO image include a blue fundus image, a green fundus image, a red fundus image, an IR fundus image, an RGB color fundus image, and an RG color fundus image. The image data for the respective UWF-SLO images are transmitted from the ophthalmic device 110 to the server 140 through the communication interface (I/F) 16F, together with patient information input through the input/display device 16E. The respective image data of the UWF-SLO image and the patient information are stored associated with each other in a storage device 254. The patient information includes, for example, patient ID, name, age, visual acuity, right eye/left eye discriminator, and the like. The patient information is input by an operator through the input/display device 16E.

An OCT system is realized by the control device 16, the OCT unit 20, and the imaging optical system 19 illustrated in FIG. 2. The OCT system is provided with the wide-angle optical system 30. This enables fundus imaging to be performed over the wide FOV 12A similarly to when imaging the SLO fundus images as described above. The OCT unit 20 includes a light source 20A, a sensor (detector) 20B, a first light coupler 20C, a reference optical system 20D, a collimator lens 20E, and a second light coupler 20F.

Light emitted from the light source 20A is split by the first light coupler 20C. After one part of the split light has been collimated by the collimator lens 20E into parallel light, to serve as measurement light, the parallel light is introduced into the imaging optical system 19. The measurement light is scanned in the X direction and the Y direction by the second optical scanner 24. The scanning light is shone onto the fundus through the wide-angle optical system 30 and the pupil 27. Measurement light that has been reflected by the fundus passes through the wide-angle optical system 30 and the second optical scanner 24 so as to be introduced into the OCT unit 20. The measurement light then passes through the collimator lens 20E and the first light coupler 20C before being incident to the second light coupler 20F.

The other part of the light emitted from the light source 20A and split by the first light coupler 20C is introduced into the reference optical system 20D as reference light, and is made incident to the second light coupler 20F through the reference optical system 20D.

The respective lights that are incident to the second light coupler 20F, namely the measurement light reflected by the fundus and the reference light, interfere with each other in the second light coupler 20F so as to generate interference light. The interference light is photo-detected by the sensor 20B. The image processing device 16G operating under the control of the CPU 16A generates OCT images, such as tomographic images and en-face images, based on OCT data detected by the sensor 20B.

OCT fundus images obtained by imaging at an imaging angle having an internal illumination angle of 160° or greater are referred to as UWF-OCT images. Obviously OCT data can be acquired at an imaging angle having an internal illumination angle of less than 160°.

The image data of the UWF-OCT images is transmitted, together with the patient information, from the ophthalmic device 110 to the server 140 though the communication interface (I/F) 16F. The image data of the UWF-OCT images and the patient information are stored associated with each other in the storage device 254.

Note that although in the present exemplary embodiment an example is given in which the light source 20A is a swept-source OCT (SS-OCT), the light source 20A may be from various types of OCT system, such as a spectral-domain OCT (SD-OCT) or a time-domain OCT (TD-OCT) system.

Next, explanation follows regarding the eye axial length measurement device 120. The eye axial length measurement device 120 has two modes, i.e. a first mode and a second mode, for measuring eye axial length, this being the length of the examined eye 12 in an eye axial direction. In the first mode light from a non-illustrated light source is guided into the examined eye 12. Interference light between light reflected from the fundus and light reflected from the cornea is photo-detected, and the eye axial length is measured based on an interference signal representing the photo-detected interference light. The second mode is a mode to measure the eye axial length by employing non-illustrated ultrasound waves.

The eye axial length measurement device 120 transmits the eye axial length as measured using either the first mode or the second mode to the server 140. The eye axial length may be measured using both the first mode and the second mode, and in such cases, an average of the eye axial lengths as measured using the two modes is transmitted to the server 140 as the eye axial length. The server 140 stores the eye axial length of the patient in association with the patient ID.

Figure 3:
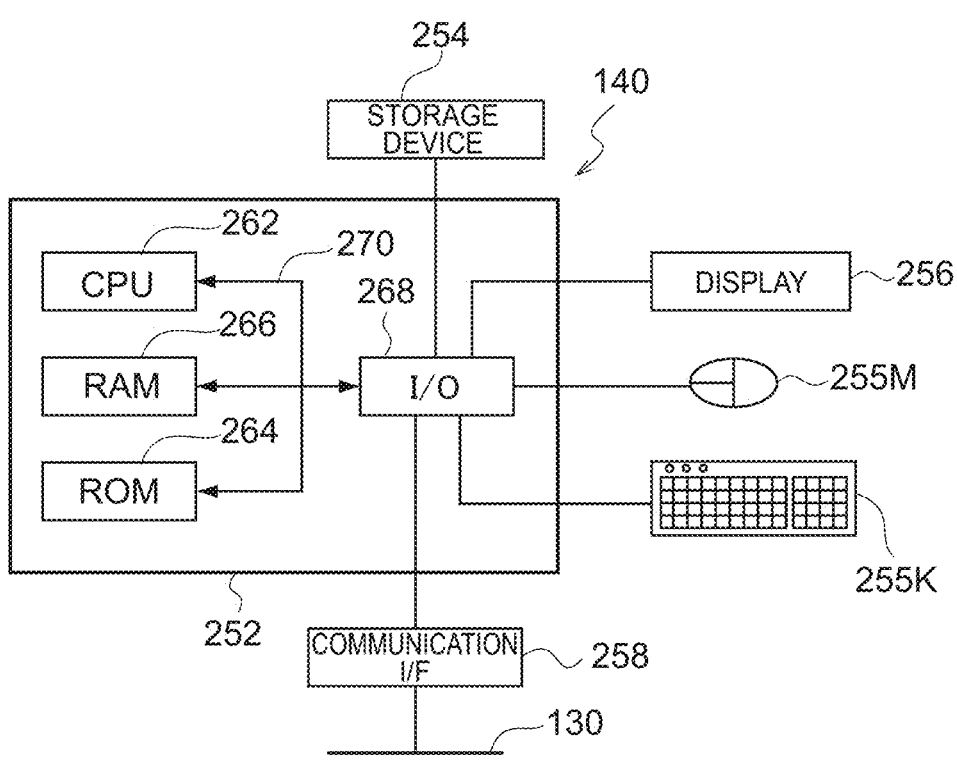
FIG. 3 is a block diagram of configuration of an electrical system of a server 140.

Explanation follows regarding a configuration of an electrical system of the server 140, with reference to FIG. 3. As illustrated in FIG. 3, the server 140 is provided with a computer body 252. The computer body 252 includes a CPU 262, RAM 266, ROM 264, and an input/output (I/O) port 268 connected together by a bus 270. The storage device 254, a display 256, a mouse 255M, a keyboard 255K, and a communication interface (I/F) 258 are connected to the input/output (I/O) port 268. The storage device 254 is, for example, configured by non-volatile memory. The input/output (I/O) port 268 is connected to the network 130 through the communication interface (I/F) 258. The server 140 is thus capable of communicating with the ophthalmic device 110 and the viewer 150. The storage device 254 is stored with an image processing program, described later. Note that the image processing program may be stored in the ROM 264.

The image processing program is an example of a "program" of technology disclosed herein. The storage device 254 and the ROM 264 are examples of "memory" and a "computer readable storage medium" of technology disclosed herein. The CPU 262 is an example of a "processor" of technology disclosed herein.

The CPU 262, described later, of the server 140 stores various data received from the ophthalmic device 110 in the storage device 254. More specifically, the CPU 262 stores respective image data of the UWF-SLO images and image data of the UWF-OCT images in the storage device 254 associated with the patient information (such as the patient ID as described above). Moreover, in cases in which there is a pathological change in the examined eye of the patient and cases in which surgery has been performed on a pathological lesion, pathology information is input through the input/display device 16E of the ophthalmic device 110, transmitted to the server 140, and stored in the storage device 254. The pathology information is stored in the storage device 254 associated with the patient information. The pathology information includes information about the position of the pathological lesion, name of the pathological change, and type of surgery and date/time of surgery etc. when surgery was performed on the pathological lesion.

The viewer 150 is provided with a computer equipped with a CPU, RAM, ROM and the like, and a display. The image processing program is installed in the ROM, and based on an instruction from a user the computer controls the display so as to display the medical information such as fundus images acquired from the server 140.

Figure 4:
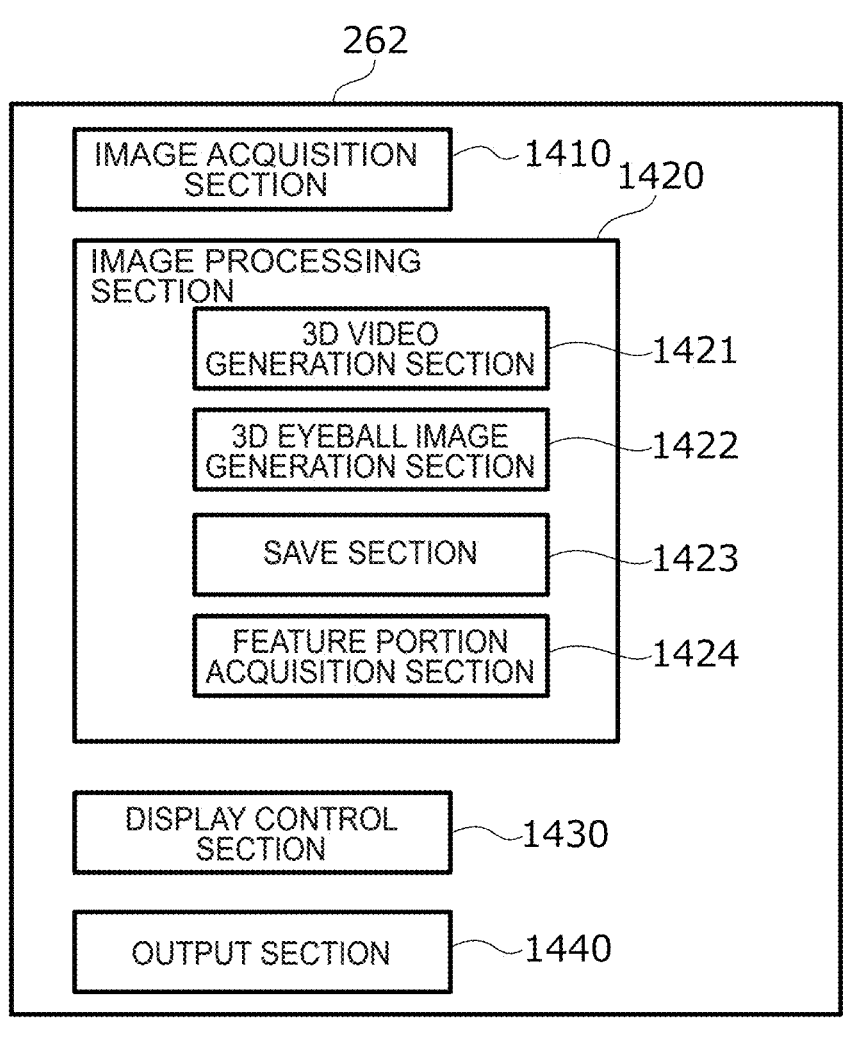
FIG. 4 is a block diagram illustrating functionality of a CPU 262 of the server 140 of a first exemplary embodiment.

Explanation follows regarding various functions implemented by the CPU 262 of the server 140 of the first exemplary embodiment executing the image processing program, with reference to FIG. 4. The image processing program includes an image acquisition function, image processing function (3D video generation function, 3D eyeball image generation function, save function, and feature portion acquisition function), display control function, and output function. By the CPU 262 executing the image processing program including these functions, the CPU 262 functions as an image acquisition section 1410, an image processing section 1420 (a 3D video generation section

1421, a 3D eyeball image generation section 1422, a save section 1423, and a feature portion acquisition section 1424), a display control section 1430, and an output section 1440, as illustrated in FIG. 4.

Figure 5:
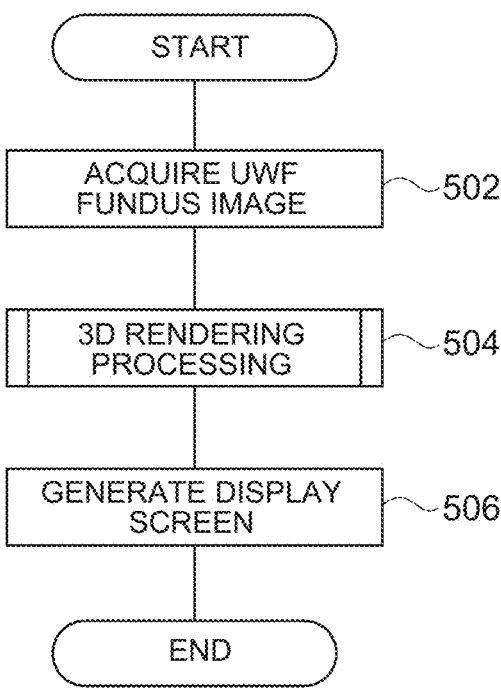
FIG. 5 is a flowchart of image processing by the server 140 of the first exemplary embodiment.

Next detailed description follows regarding image processing by the server 140, with reference to FIG. 5. The image processing illustrated in the flowchart of FIG. 5 is implemented by the CPU 262 of the server 140 executing the image processing program. This image processing is started when a UWF fundus image (UWF-SLO image) is acquired by the ophthalmic device 110 and transmitted together with the patient ID to the server 140, and the server 140 has received the patient ID and the UWF fundus image.

At step 502 the image acquisition section 1410 acquires a UWF fundus image G1 corresponding to the patient ID from the storage device 254. The UWF fundus image G1 is, for example, a RGB color fundus image (see FIG. 7A).

At step 504 the image processing section 1420 executes 3D rendering processing (see also FIG. 6), described in detail later, on the UWF fundus image G1.

At step 506 the display control section 1430 generates a display screen (see also FIG. 12, FIG. 14, and FIG. 15), described in detail later.

Figure 6:
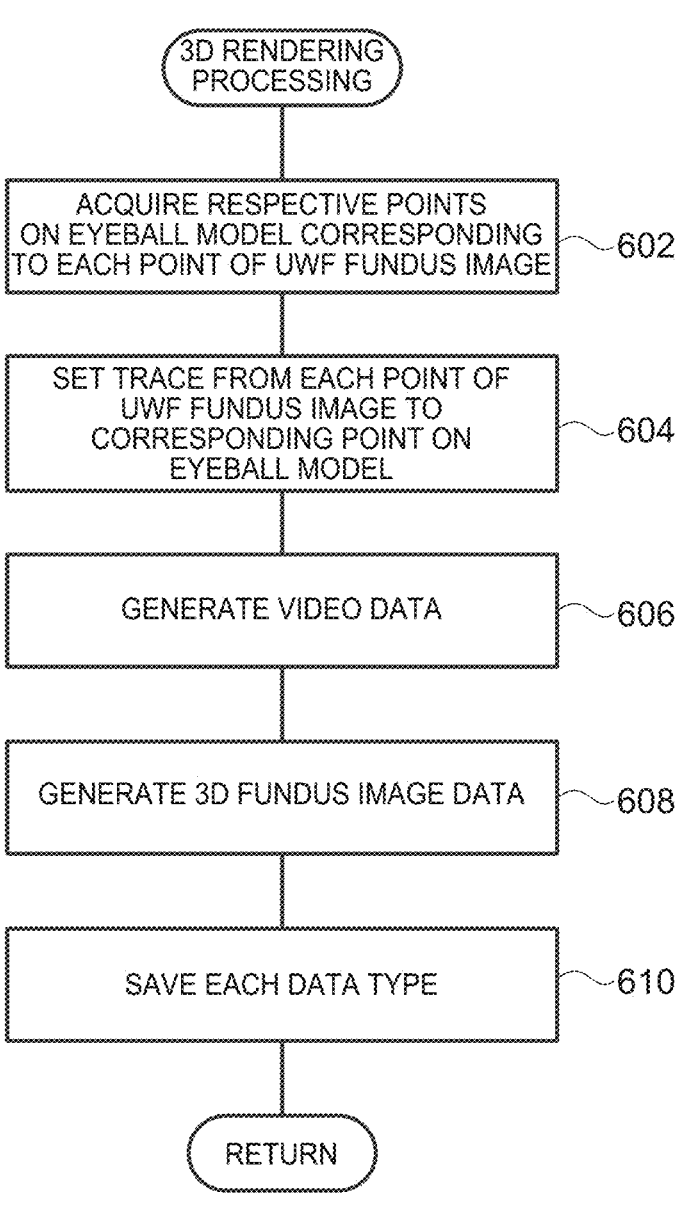
FIG. 6 is a flowchart of 3D rendering processing of step 504 of FIG. 5.

Next, description follows regarding the 3D rendering processing of step 504, with reference to FIG. 6.

At step 602 the 3D video generation section 1421 acquires respective points on an eyeball model M corresponding to each of the points of the UWF fundus image G1.

Figure 8:
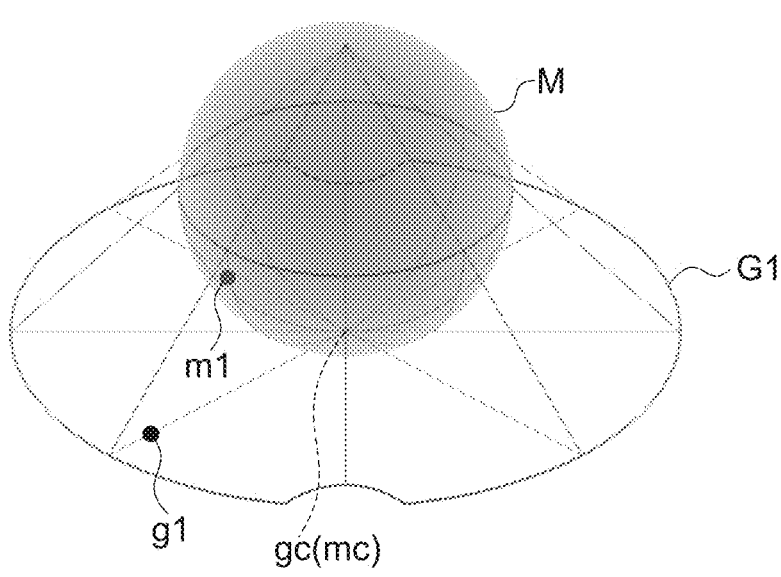
FIG. 8 is a diagram illustrating a point g1 of a UWF fundus image G1 and a point m1 on an eyeball model M corresponding to the point g1.

More specifically, the 3D video generation section 1421 generates video data configured from plural frames to represent a process of projecting the UWF fundus image G1 onto the eyeball model M, as illustrated in FIG. 8. A method of projecting a spherical surface onto a flat plane is stereographic projection, however in the present exemplary embodiment the 3D video generation section 1421 generates video data to represent a process of reverse stereographic projection from a flat plane onto a spherical surface.

More specifically, the 3D video generation section 1421 first performs positional alignment between the UWF fundus image G1 and the eyeball model M. Specifically the 3D video generation section 1421 arranges such that a projection center of the UWF fundus image G1 is aligned with a projection center of the eyeball model M, and a projection plane from the center of the eyeball model M is horizontal. The XY directions taking a center gc of the UWF fundus image G1 as the center are aligned with the XY directions taking a pupil center me of the eyeball model M as the center.

After positional alignment between the eyeball model M and the UWF fundus image G1 is finished, the 3D video generation section 1421 sets zero for a variable g related to a time step to identify each of the points of the UWF fundus image G1, increments the variable g by one, and transforms a point on the UWF fundus image G1 as identified by the variable g into a point on the eyeball model M according to the following transformation equation. A point on the eyeball model M is accordingly acquired that corresponds to the point on the UWF fundus image G1 identified by the variable g. In the present Example the UWF fundus image G1 is arranged in a flat plane of Z=−1. The following transformation equation is employed, wherein points on the UWF fundus image G1 are denoted by (Xg, Yg, −1), points on the eyeball model M corresponding to the UWF fundus image G1 points (Xg, Yg, −1) are denoted by (Xmg, Ymg, Zmg).

$$Xmg=4Xg/(4+Xg^2+Yg^2)$$

$$Ymg=4Yg/(4+Xg^2+Yg^2)$$

$$Zmg=(-4+Xg^2+Yg^2)/(4+Xg^2+Yg^2)$$

For example, as illustrated in FIG. 8, a point g1 (X1, Y1, −1) of the UWF fundus image G1 identified by variable g=1 is transformed into a point m1 (Xm1, Ym1, Zm1) on the eyeball model M. The above transformation is executed for all of the points on the UWF fundus image G1. The point g1 is set for each of the pixels of the UWF fundus image G1. The above transformation is executed for all of the pixels of the UWF fundus image G1.

Note that instead of the above transformation being performed for each point (pixel) of the UWF fundus image G1, a user may perform the above transformation on a region selected by the user to include a pathological change of the UWF fundus image G1, such as a detached retina, or a region including a vortex vein.

A default eyeball model may be employed as the eyeball model employed at step 602. However, in the present exemplary embodiment the 3D video generation section 1421 reads the eye axial length corresponding to the patient ID from the storage device 254, and pre-corrects the size of the default eyeball model according to the read eye axial length.

Moreover, in the present exemplary embodiment the 3D video generation section 1421 uses the transformation equation to acquire the points on the eyeball model M corresponding to each of the points of the UWF fundus image G1. The technology disclosed herein is not limited thereto. A transformation lookup table may be prepared in advance for the eyeball model, and the 3D video generation section 1421 may acquire points on the eyeball model M corresponding to each of the points of the UWF fundus image G1 by reference to this table.

At step 604 the 3D video generation section 1421 acquires a trace for a pixel at each of the points on the UWF fundus image to move to each of the corresponding points on the eyeball model.

More specifically, the 3D video generation section 1421 sets variable g to zero, increments variable g by one, and sets as a path a line connecting the point on the UWF fundus image G1 identified by the variable g to the point on the eyeball model M corresponding to this point. The 3D video generation section 1421 computes a position at each specific time of a pixel of the point on the UWF fundus image G1 identified by the variable g. Note that the specific time is a time according to a frame rate of video data as described later.

For a pattern of the above movement there are plural patterns differing by at least one out of path of movement of the pixel at each point on the UWF fundus image G1 or movement speed.

The path referred to above may be a straight line or a curve, however a straight line is employed in the present exemplary embodiment. Note that a user may be given a selection from out of a straight line or a curve (for example, plural upward convex curves of different curvature, plural downward convex curves of different curvature).

Moreover, the speed may be fixed or varied during movement. In the present exemplary embodiment the speed is fixed at a predetermined speed V0 during movement. For the speed too, an operator may be given a selection from out of a constant speed (plural speeds), plural patterns gradually getting faster, plural patterns gradually getting slower, and the like.

Figure 9:
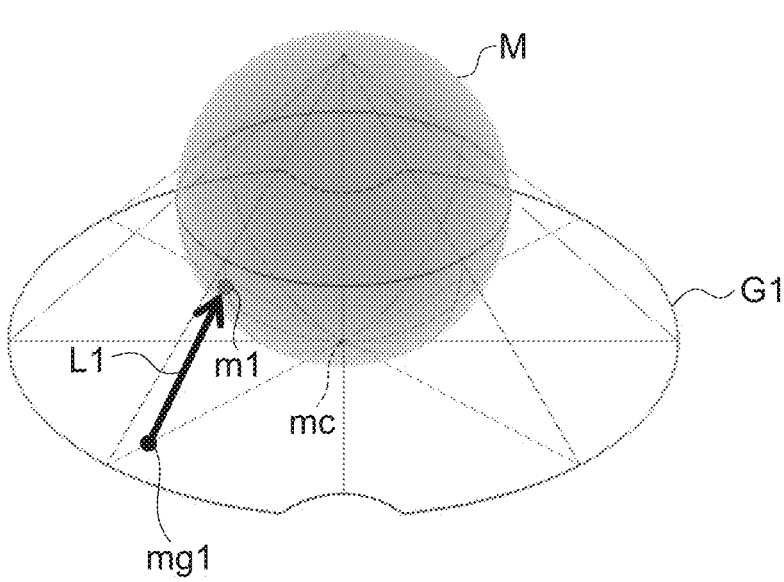
FIG. 9 is a diagram illustrating a path L1 along which a pixel at a point mg1 of an UWF fundus image G1 moves to a point m1 on an eyeball model M corresponding to a point g1.
Figure 13:
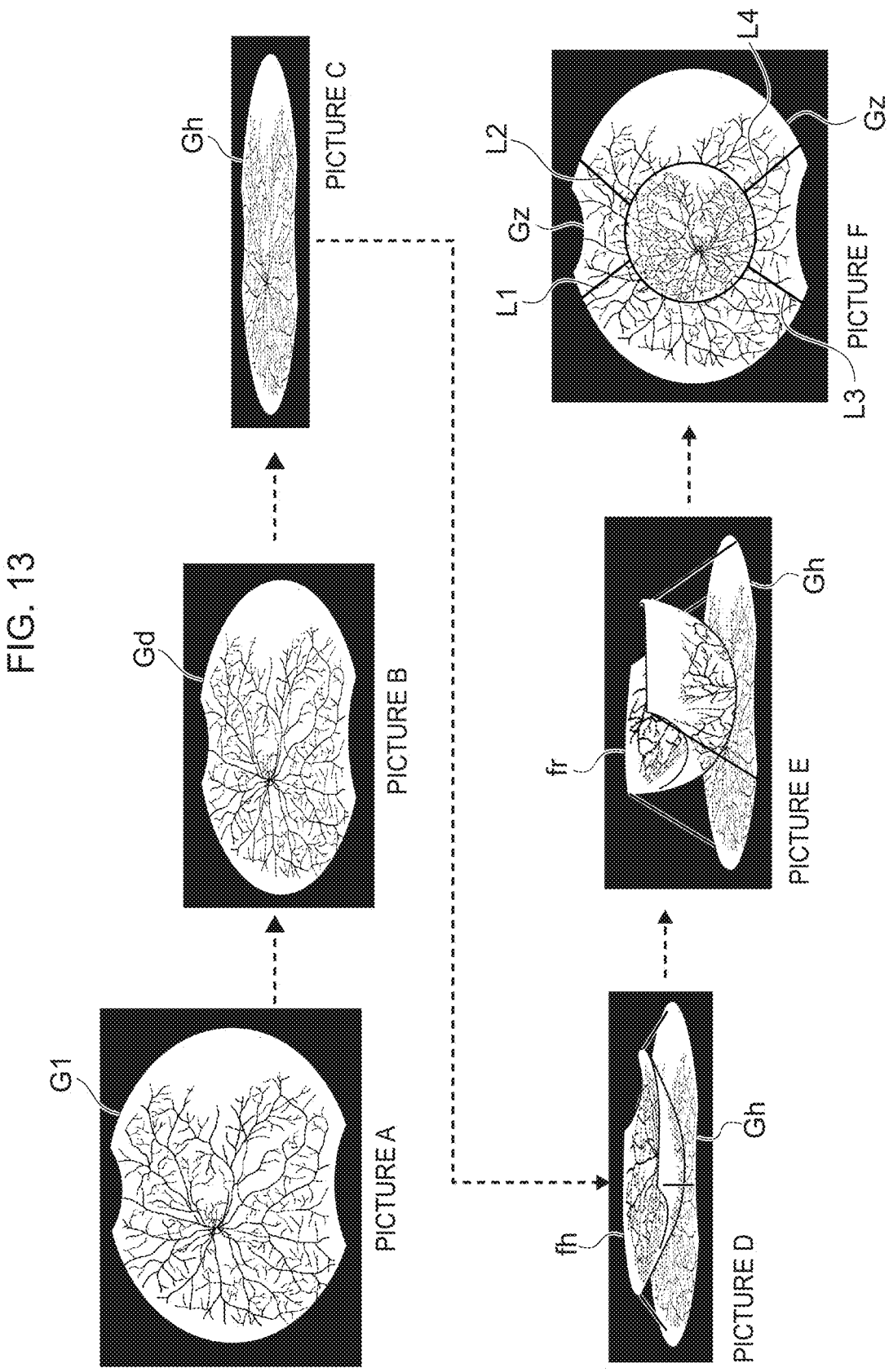
FIG. 13 is a diagram illustrating images displayed on a video data display section 455A.

More specifically, for example, for variable g=1, the 3D video generation section 1421 may transform a point g1 on the UWF fundus image G1 identified by variable g=1 to a point mg1 in an XYZ coordinate system of the eyeball model M, as illustrated in FIG. 9, by transforming point g1 coordinate (X1, Y1) to point mg1 coordinate (X1, Y1, −1). Generally in a stereographic projection transformation the UWF fundus image G1 is arranged at Z=0, however in this case the UWF fundus image G1 is intentionally arranged at Z=−1 to generate a transformation video while leaving the UWF fundus image G1 untouched, as illustrated in FIG. 13.

The 3D video generation section 1421 sets a line segment L1 for point mg1 (X1, Y1, −1) and point m1 (Xm1, Ym1, Zm1) in the XYZ coordinate system.

As described later, in the present exemplary embodiment video data is created to represent a process to move the pixel of point mg1 (X1, Y1, −1) to point m1 (Xm1, Ym1, Zm1). When the video data is replayed, the pixel at point mg1 (X1, Y1, −1) is displayed as moving along the line segment L1 to the point m1 (Xm1, Ym1, Zm1). Thus the line segment L1 is a trace of movement of the pixel of point mg1 (X1, Y1, −1). Note that the line segment L1 is also called path L1.

Figure 10:
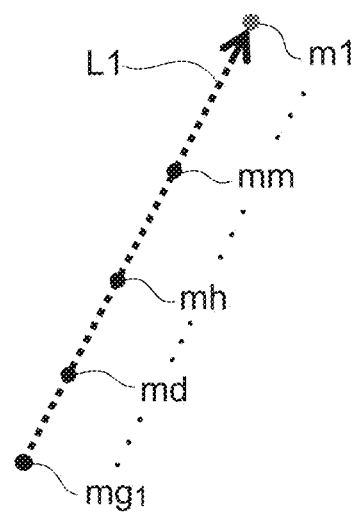
FIG. 10 is a diagram illustrating a way in which a pixel at a point mg1 of an UWF fundus image G1 moves at a constant speed V0 along the path L1 to points md, . . . , mh, . . . mm, . . . m1.

In the present exemplary embodiment, a pattern of constant speed straight line movement is predetermined for pixels at all of the points on the UWF fundus image G1 to move along the corresponding paths to respective points on the eyeball model M corresponding to each pixel point. This pattern is, for example, as illustrated in FIG. 10, moving a pixel at point mg1 (X1, Y1, 0) at the constant speed V0 along path L1 to the points md, . . . , mh, . . . mm, . . . m1. The 3D video generation section 1421 computes the position (XYZ coordinate system) at each specific time of the pixel at point mg1 (X1, Y1, −1) from the path L1 and the speed V0.

The 3D video generation section 1421 executes the above processing until variable g reaches the total number of points on the UWF fundus image G1. Positions along a movement path are thereby acquired for pixels at all points on the UWF fundus image G1.

Note that the movement pattern may be different for every pixel at each point of the UWF fundus image G1. For example, a pixel at a given point on the UWF fundus image G1 may have a movement of a constant speed in a straight line, whereas a pixel at another point may move along an upward convex curved path at a gradually slowing speed.

At step 606 the 3D video generation section 1421 generates video data to represent a process to move pixels at all points on the UWF fundus image G1 to the respective points on the eyeball model M corresponding to these pixel points.

Figure 11:
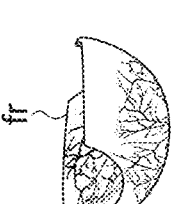
FIG. 11 is a diagram illustrating respective frames of video data.

Specifically, first using each pixel of the UWF fundus image G1 as a data point, an initial frame is generated with these data points arranged in an XY plane Z=−1 in a three-dimensional coordinate system (processing corresponding to f1 in FIG. 11, wherein FIG. 11 is a diagram to explain plural frames of video data).

Next these data points are arranged at a positions after a specific time (Δt) has elapsed from the trace data set at step 604. A flat plane (curved plane) is defined by arranging these data points for all of the data points of the UWF fundus image G1. Pixel data (color and brightness data) is input for data points in this flat plane, and intermediate frames are generated for after specific times (Δt) have elapsed (corresponding to fd, fh, fm of FIG. 11).

The generation of intermediate frames continues and frame creation is repeated in a similar manner from specific times Δt1 to Δtn (wherein n is a frame number for generating frames up to a final position n). fn is the final frame in FIG. 11, and is a frame of a state in which all the data points have moved to their respective points on the eyeball model M.

After completing frames 1 to n, frame numbers, a video file number, and the like are appended, and video data is generated.

A linear interpolation, spline interpolation, or the like may be employed as the method of computing a flat plane. A surface model, a spatial lattice model, or the like may be employed as a flat plane geometric model. Without computing a flat plane, the data points may be given a size and displayed as a scatter diagram.

In the present exemplary embodiment as described above, the pixel at all points on the UWF fundus image G1 are moved along path L at constant speed V0 in a predetermined constant speed straight line movement pattern to the respective points on the eyeball model M corresponding to these pixel points. Thus at step 606, as video data, plural frames (still images) are each generated for each of the specific times to represent the constant speed straight line movement of the pixels for all points on the UWF fundus image G1 to the points on the eyeball model M corresponding to these pixel points.

For example, as illustrated in FIG. 11, a first frame f1 matches the UWF fundus image G1. The 3D video generation section 1421 generates frames for specific times afterwards by arranging each of the corresponding pixels at its position after the calculated movement. By repeating the above processing, the 3D video generation section 1421 generates frames fd, . . . , fh, . . . , fm, . . . fr at each of the specific times until the pixels at all points on the UWF fundus image G1 have moved to the points on the eyeball model M corresponding to these pixel points, as illustrated in FIG. 11.

At step 608 the 3D eyeball image generation section 1422 generates 3D eyeball image data.

3D eyeball image data is image data of an eyeball image obtained by transforming the UWF fundus image G1 so as to be stuck onto a specific eyeball model, and is obtained by combining an anterior eye portion image, such as of the iris, lens body, and the like, with the transformed UWF fundus image G1. The 3D eyeball image generation section 1422 may take the image after the pixels at all points on the UWF fundus image G1 have been moved to the points on the eyeball model M corresponding to these pixel points (the final frame of the video) as the 3D eyeball image.

In separate processing to the image processing of FIG. 5, the feature portion acquisition section 1424 acquires information about a feature portion. Examples of a feature portion include, as fundus structures, blood vessels (for example, retinal blood vessels, choroidal blood vessels, etc.), an optic nerve head, a macular, a vortex vein, or the like. The 3D eyeball image generation section 1422 generates 3D eyeball image data by taking an image after the pixels at all points on the UWF fundus image G1 have been moved to the points on the eyeball model M corresponding to these pixel points, and emphasizing an image of feature portions acquired by the feature portion acquisition section 1424. The feature portion may also encompass a pathological lesion. Pathological lesions are identified by examination by an ophthalmologist. For example, a mark indicating a region including a detached retina is displayed overlaid on the UWF fundus image G1.

Coordinate data on the UWF fundus image G1 is taken for the positions and regions of such feature objects, and names of pathological changes and names of feature objects are combined with the coordinate data and saved in the storage device 254.

When creating the video data, video data may be created at step 606 from the UWF fundus image G1 marked with the positions of feature objects and pathological changes.

At step 610, the save section 1423 saves (stores) each data type (video data and 3D fundus image data) in the storage device 254.

After the saving processing at step 610 has finished for each data type, the 3D rendering processing of step 504 of FIG. 5 is ended, and image processing proceeds to step 506 where the display control section 1430 generates a display screen (see also FIG. 12, FIG. 14, and FIG. 15), and the image processing is then ended.

A user (such as an ophthalmologist) inputs the patient ID into the viewer 150 when examining the examined eye of the patient. The viewer 150 instructs the server 140 to transmit examined eye image data corresponding to the patient ID, and so on. The output section 1440 of the server 140 transmits the patient name, patient age, patient visual acuity, left eye/right eye information, eye axial length, imaging date, image data, and so on corresponding to the patient ID to the viewer 150 together with the patient ID.

The image data etc. includes UWF fundus images, video data, 3D fundus image data, and information about feature portions.

Figure 12:
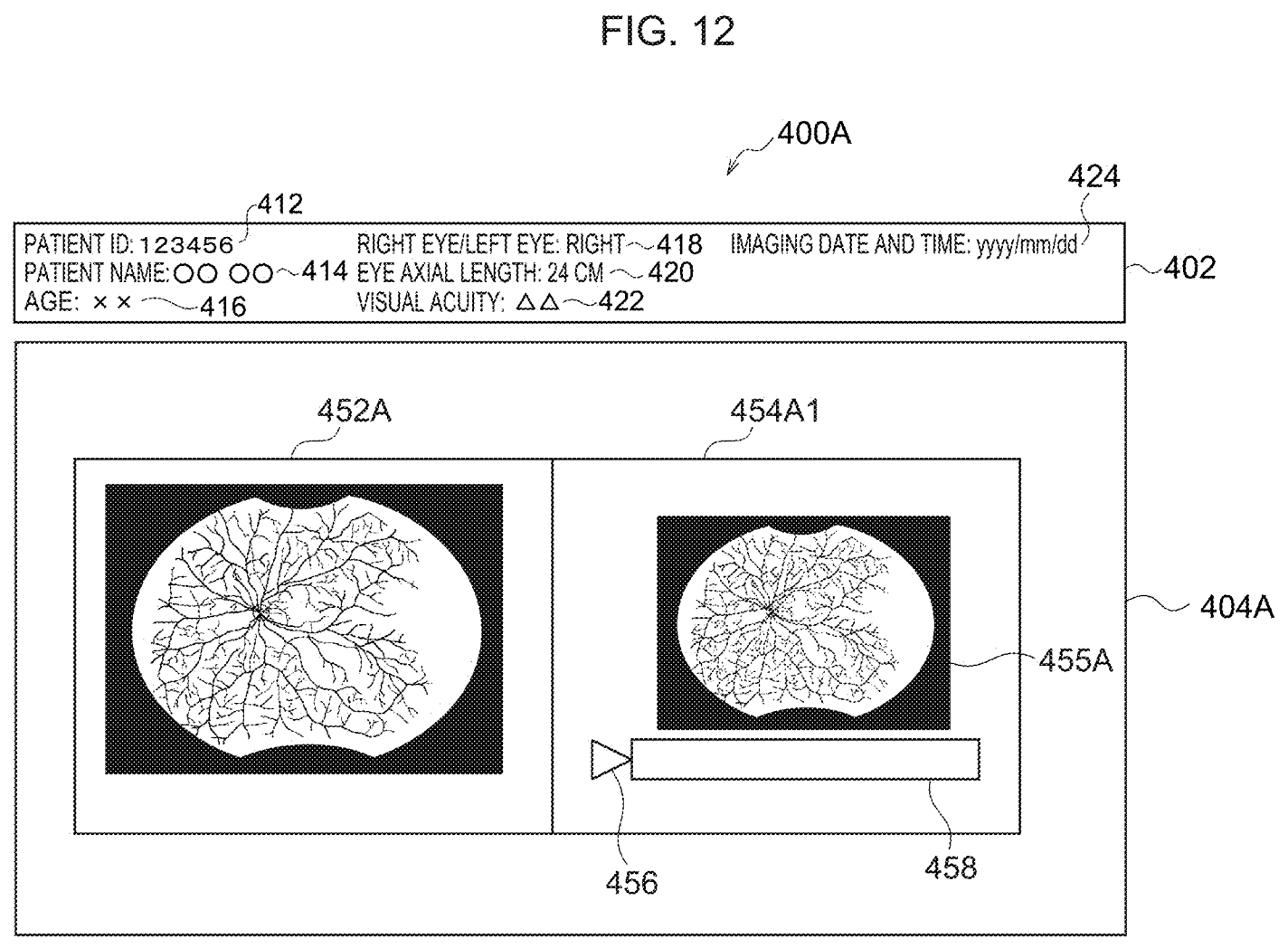

On receiving the patient ID, patient name, patient age, patient visual acuity, left eye/right eye information, eye axial length, imaging date, and image data, the viewer 150 displays a display screen 400A illustrated in FIG. 12 on the display.

As illustrated in FIG. 12, the display screen 400A includes an information display area 402 and an image display area 404A.

The information display area 402 includes a patient ID display field 412, a patient name display field 414, an age display field 416, a left eye/right eye display field 418, an eye axial length display field 420, a visual acuity display field 422, and an imaging date and time display field 424. The viewer 150 displays various information in the respective display fields from the patient ID display field 412 to the imaging date and time display field 424 based on the received information.

The image display area 404A includes an SLO image display field 452A and a video data display field 454A1. The video data display field 454A1 includes a video data display section 455A, a replay button 456, and a display progress display section 458.

The UWF fundus image is displayed in the SLO image display field 452A. The video data is displayed on the video data display section 455A when the replay button 456 is operated, and a portion corresponding to the proportion already displayed from out of the entire video data is infilled in a specific color in the display progress display section 458.

Explanation follows regarding replay of the video data on the video data display section 455A. The UWF fundus image G1 such as illustrated in FIG. 12 and FIG. 13 is displayed prior to operating the replay button 456.

When the replay button 456 is operated, first a face-on view of the UWF fundus image G1 is displayed (picture a), then an image Gd of the UWF fundus image G1 tilted by a specific angle is displayed (picture b), then a perspective view image Gh of the UWF fundus image G1 further tilted is displayed (picture c), as illustrated in FIG. 13. The process during which the picture a, picture b, and the picture c are displayed is a first process to transform a face-on view of a two-dimensional fundus image into a perspective view.

Then while the image Gh is left as is, a picture d is displayed in which a three-dimensional fundus image fh exhibiting an initial state of reverse stereographic projection transformation is displayed overlaid on the image Gh. Pictures are displayed to represent the manner of reverse stereographic projection transformation, more specifically the first frame f1, . . . , frame fh, . . . , frame fr are displayed. Then a picture e is displayed, in which a three-dimensional image fr exhibiting the completed state of reverse stereographic projection transformation is displayed overlaid on the image Gh. The process during which picture d to picture e are displayed is a second process a three-dimensional fundus image is displayed changing as it is subjected to reverse stereographic projection transformation on a two-dimensional fundus image in horizontal view.

Finally, the picture e is rotated, and an image Gz is displayed with a face-on view of the three-dimensional fundus image fr overlaid on the face-on view of the UWF fundus image G1 (picture f). The process of displaying from picture e to picture f is a third process of rotating an integrated image of the horizontal view of the two-dimensional fundus image together with a three-dimensional fundus image after transformation completion.

Note that the video data may, as illustrated in FIG. 11, be a video merely of the process of reverse stereographic projection transformation on the UWF fundus image G1 (i.e. not a video in which the image Gh remains as is as in FIG. 13, but a video in which the image Gh does not remain).

In cases in which the video data is displayed, the paths of the points are displayed from predetermined points, which in the example illustrated in FIG. 13 are four pre-selected points outermost in the upward and downward directions (L1, L2, L3, L4 in the diagram). Moreover, the paths of positions of the above mentioned feature portions, such as vortex veins, detached retina, or the like, may be displayed.

Figure 14:
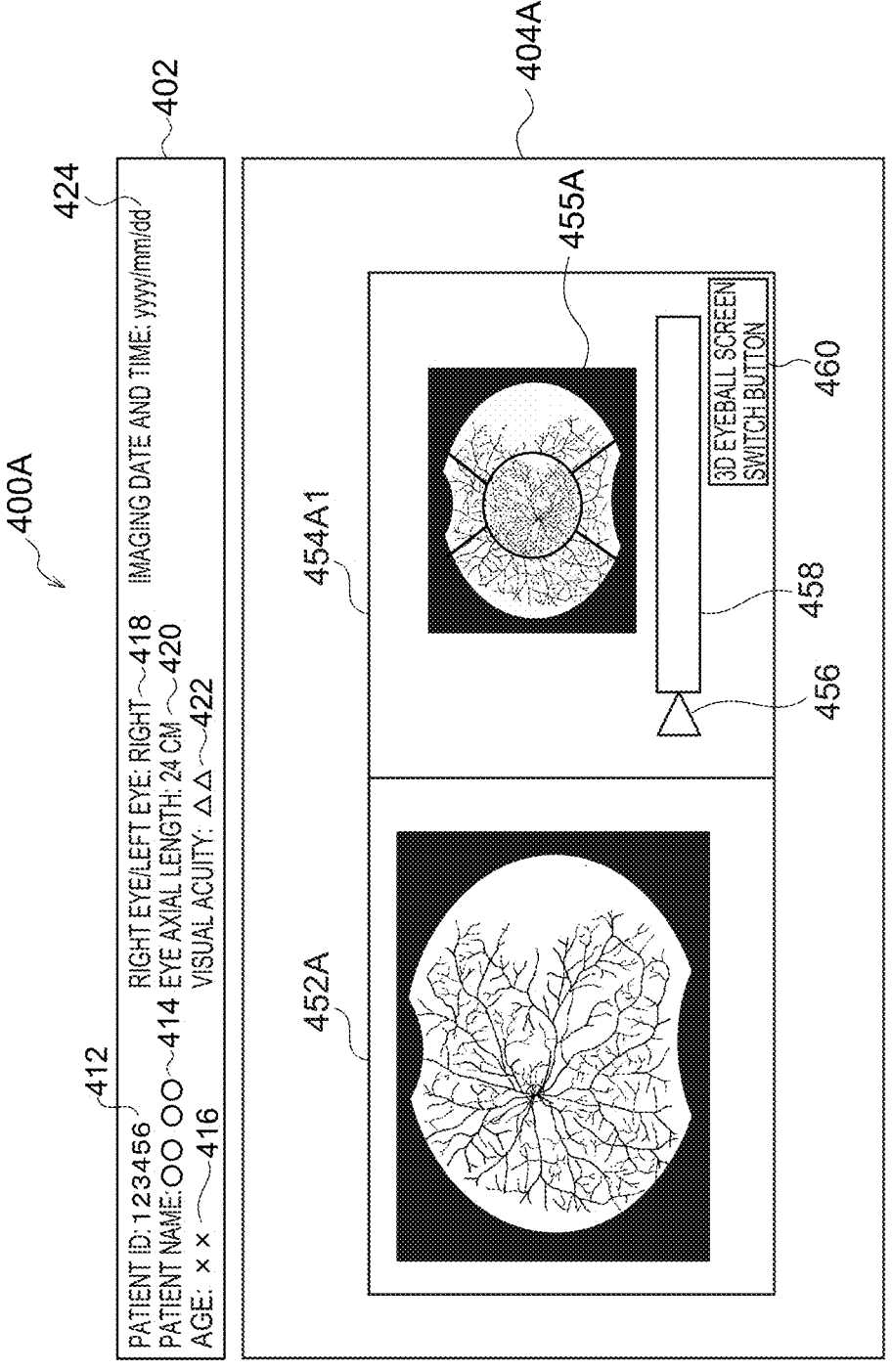
FIG. 14 is a diagram illustrating a second display pattern of the display screen 400A.

When the video data is displayed in the video data display section 455A and the image Gz is displayed, as illustrated in FIG. 14, a 3D eyeball image switch button 460 is displayed in the video data display field 454A1.

Figure 15:
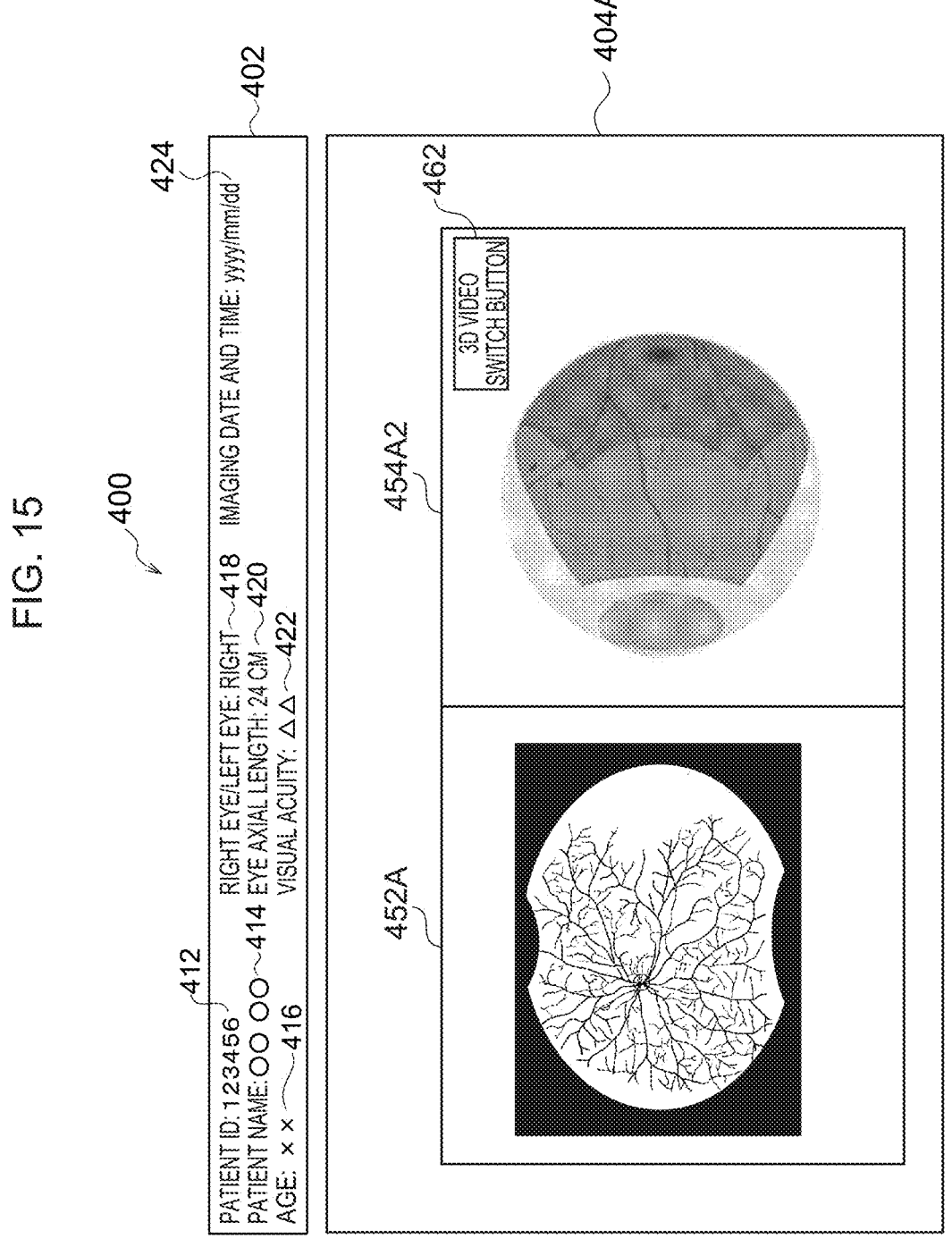
FIG. 15 is a diagram illustrating a third display pattern of the display screen 400A.

When the 3D eyeball image switch button 460 is operated, as illustrated in FIG. 15, the video data display field 454A1 is switched to a 3D fundus image display field 454A2. The 3D eyeball image is displayed in the 3D fundus image display field 454A2. As described above, the image data is of an image of an eyeball obtained by transforming the UWF fundus image G1 so as to be stuck onto a specific eyeball model, and by combining an anterior eye portion image, such as of the iris, lens body, and the like, with the transformed UWF fundus image G1.

A 3D video switch button 462 is displayed in the 3D fundus image display field 454A2. A switch is made to the display screen 400A of FIG. 12 when the 3D video switch button 462 is operated.

As explained above, the first exemplary embodiment creates video data to represent a process to move pixels at each point of the UWF fundus image to respective corresponding points on the eyeball model. This enables a user to know the manner in which each point on the UWF fundus image moves to each of the corresponding points on the eyeball model. A user is accordingly able to know which point of the corresponding points on the eyeball model is which point on the UWF fundus image.

Thus by a user (ophthalmologist) viewing the video data generated from the UWF fundus image, the user is able to directly ascertain a position and size of a pathological change (surface area of a pathological lesion) on the eyeball at fundus peripheral portions and fundus equatorial portions. Moreover, the ophthalmologist is able to easily explain the examination results, such as the position and size of a pathological change, to the examinee (patient).

Moreover, the first exemplary embodiment illustrates a case in which a video is generated of a process of transforming a two-dimensional UWF fundus image into a three-dimensional fundus image based on an eyeball model. However, there is no limitation thereto, and a video may be generated of a process of transforming an image of an anterior eye portion imaged in two dimensions into a three-dimensional anterior eye portion image based on an eyeball model. For example, a video may be generated for transformation of a two-dimensional flat plane image of a lens body based on a three-dimensional lens body model. This can be used to easily ascertain sites of the lens body such as the pigmentation and the like in a three-dimensional manner, and can be used for planning of a procedure for glaucoma surgery.

Second Exemplary Embodiment

Next, description follows regarding a second exemplary embodiment of the technology disclosed herein. The configuration of the second exemplary embodiment is substantially similar to the configuration of the first exemplary embodiment, and so only differing parts (a fixation function of the ophthalmic device 110 and montage image generation of the server 140) will be described.

First explanation follows regarding the fixation function of the ophthalmic device 110 of the second exemplary embodiment.

The imaging device 14 of the ophthalmic device 110 includes a fixation target control device to illuminate a non-illustrated upper fixation lamp and lower fixation lamp (further including a non-illustrated central fixation lamp) under control of the control device 16. The orientation (gaze direction) of the examined eye 12 can be changed by illuminating one or other out of the central fixation lamp, the upper fixation lamp, or the lower fixation lamp.

Next, description follows regarding a montage image generation function implemented by the CPU 262 of the server 140 of the second exemplary embodiment executing an image processing program.

Figure 16:
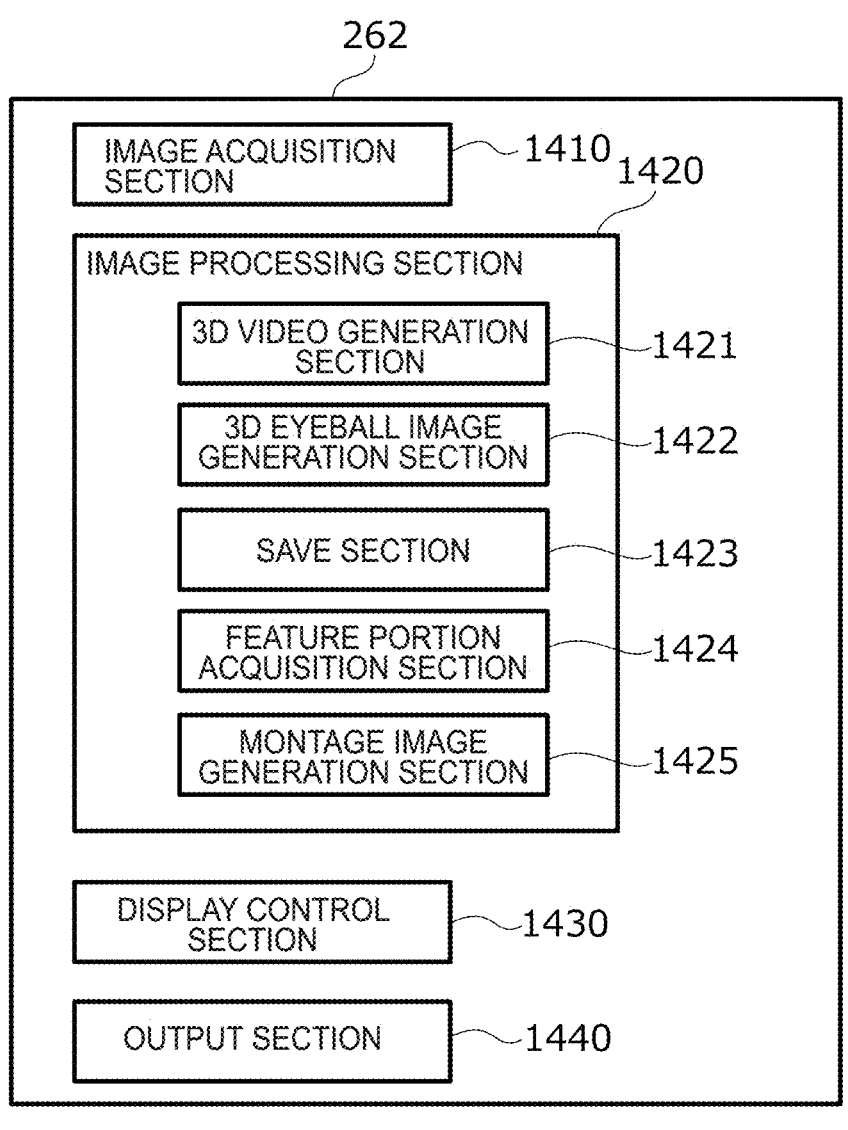
FIG. 16 is a block diagram illustrating functionality of a CPU 262 of a server 140 of a second exemplary embodiment.

FIG. 16 is a block diagram illustrating various functions implemented by the CPU 262 of the server 140 of the second exemplary embodiment executing the image processing program. The image processing program of the second exemplary embodiment has, in comparison to the first exemplary embodiment, a montage image generation function added to the image processing function. Thus by the CPU 262 executing the image processing program including these functions, the CPU 262 further functions as a montage image generation section 1425.

The ophthalmic device 110 controls the fixation target control device to illuminate the upper fixation lamp in order to shift the gaze of the patient to face diagonally upward. The gaze of the patient is thereby facing diagonally upward, namely, facing in a direction from the center of the eyeball toward the upper fixation lamp. Rather than by illuminating the upper fixation lamp, the gaze of the examined eye may also be placed in a diagonally upward facing state by the operator of the ophthalmic device 110 giving an instruction for the patient to gaze diagonally upward, such as "please look up".

The ophthalmic device 110 images the fundus in the upward looking state in which the gaze of the patient is facing diagonally upward. An UWF upward looking fundus image GU is obtained (see also FIG. 19A).

The ophthalmic device 110 controls the fixation target control device to illuminate the lower fixation lamp in order to shift the gaze of the patient to face diagonally downward. The gaze of the patient is thereby facing diagonally downward, namely, facing in a direction from the center of the eyeball toward the lower fixation lamp. Rather than by illuminating the lower fixation lamp, the gaze of the examined eye may also be placed in a diagonally downward facing state by the operator of the ophthalmic device 110 giving an instruction for the patient to gaze diagonally downward, such as "please look down".

The ophthalmic device 110 images the fundus in the downward looking state in which the gaze of the patient is facing diagonally downward. An UWF downward looking fundus image GD is obtained thereby. Note that FIG. 19B illustrates a UWF downward looking fundus image GDC that has been positionally aligned, described later.

Examples of the UWF upward looking fundus image GU include, similarly to the first exemplary embodiment, a blue fundus image (UWF upward looking fundus image B), a green fundus image (UWF upward looking fundus image G), a red fundus image (UWF upward looking fundus image R), an IR fundus image (UWF upward looking fundus image IR), an RGB color fundus image (UWF upward looking fundus image RGB), and an RG color fundus image (UWF upward looking fundus image RG).

Similarly with the UWF downward looking fundus image GD, there is a blue fundus image (UWF downward looking fundus image B), a green fundus image (UWF downward looking fundus image G), a red fundus image (UWF downward looking fundus image R), an IR fundus image (UWF downward looking fundus image IR), an RGB color fundus image (UWF downward looking fundus image RGB), and an RG color fundus image (UWF downward looking fundus image RG).

The UWF upward looking fundus image GU and the UWF downward looking fundus image GD are transmitted to the server 140 by the ophthalmic device 110 and stored in the storage device 254.

Figure 17:
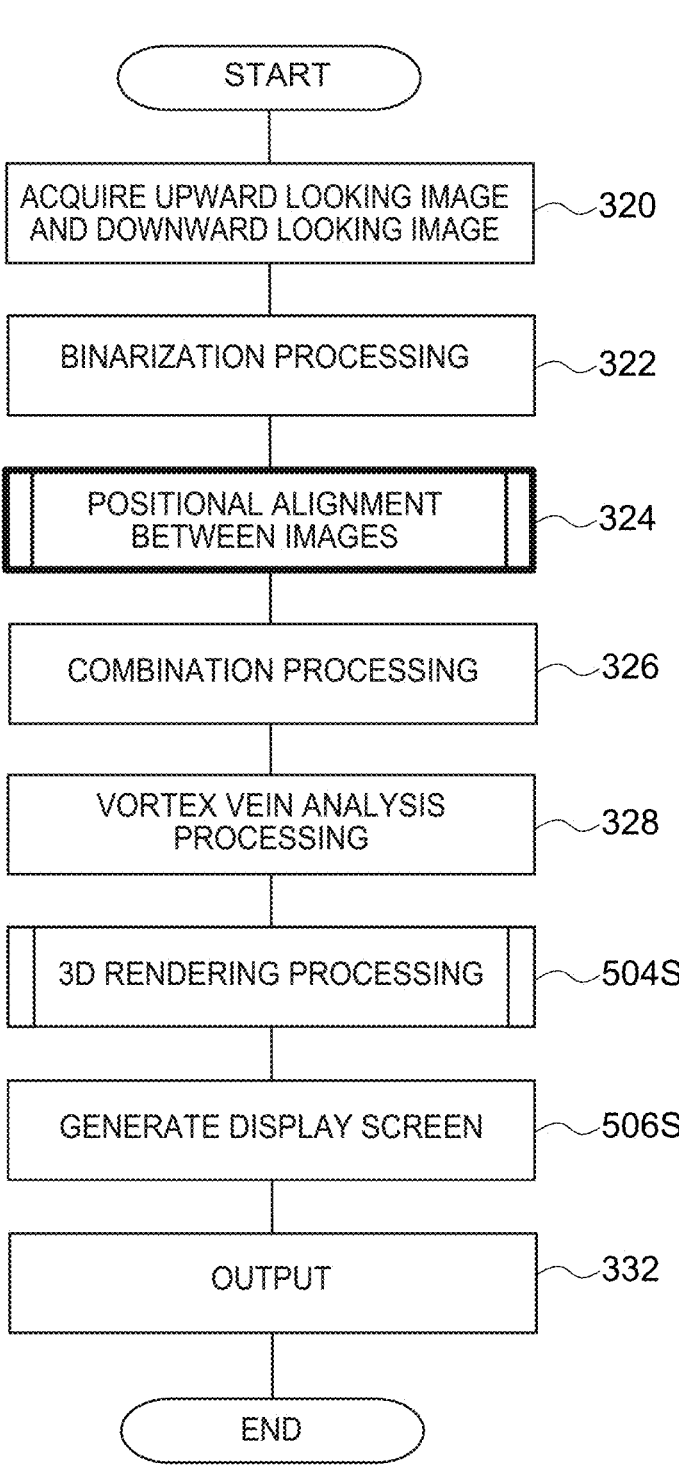
FIG. 17 is a flowchart of image processing by the server 140 of the server 140 of the second exemplary embodiment.

FIG. 17 illustrates a flowchart of image processing of the second exemplary embodiment. The image processing of the second exemplary embodiment is started when the server 140 has received the UWF upward looking fundus image GU and the UWF downward looking fundus image GD.

At step 320 the image acquisition section 1410 acquires the UWF upward looking fundus image and the UWF downward looking fundus image from the storage device 254. At step 322 the montage image generation section 1425 performs processing to emphasize blood vessels in the UWF upward looking fundus image and in the UWF downward looking fundus image. Then binarization processing is executed so as to binarize with respect to a specific threshold. The blood vessels of the fundus are emphasized in white by this binarization processing.

At step 324 the montage image generation section 1425 performs positional alignment of the UWF upward looking fundus image and the UWF downward looking fundus image. Explanation follows regarding the positional alignment processing of step 324, with reference to the flowchart of FIG. 18. Explanation follows taking an example of a case in which the UWF downward looking fundus image is transformed while the UWF upward looking fundus image is used for reference (namely, a case in which the UWF upward looking fundus image is not transformed and transformation is only performed on the UWF downward looking fundus image).

Figure 18:
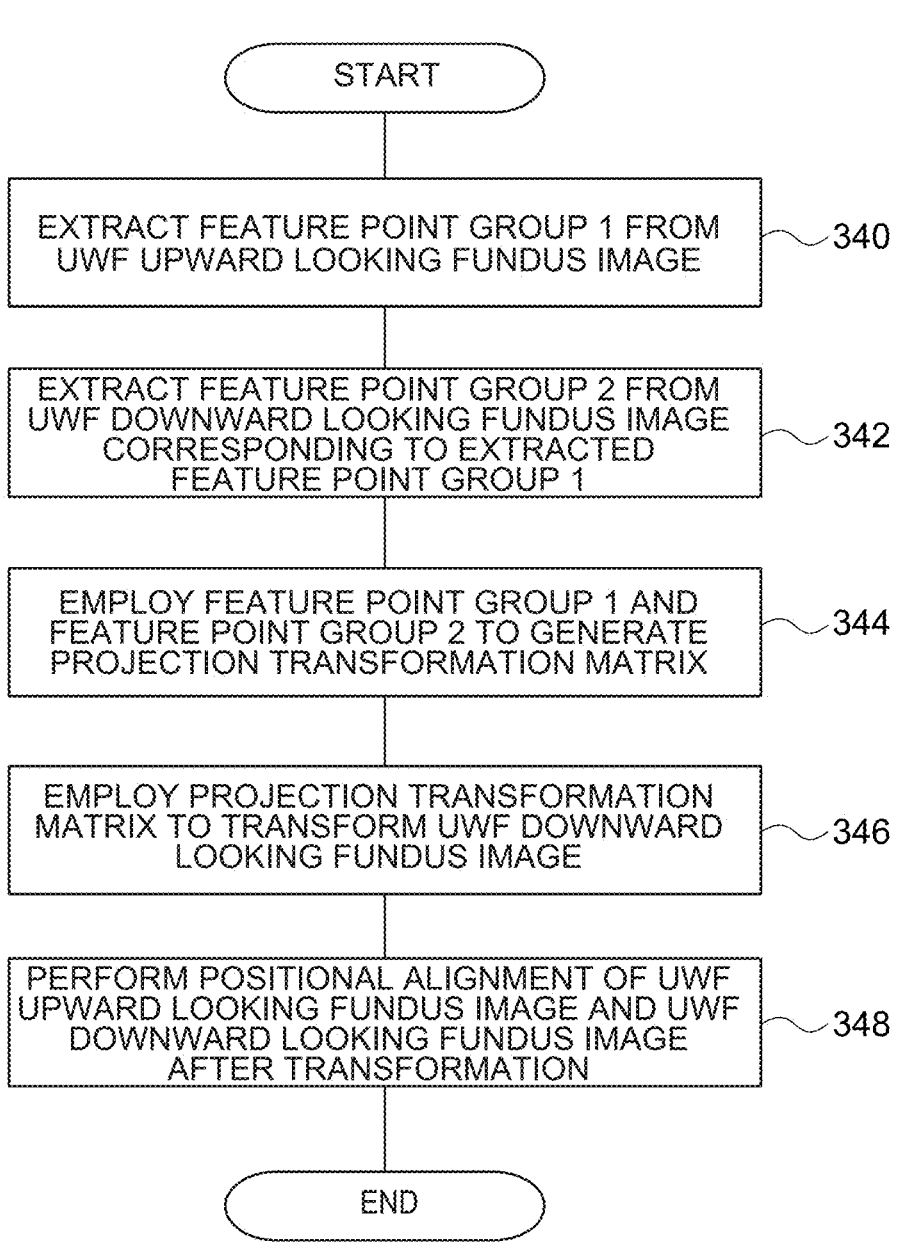
FIG. 18 is a flowchart of positional alignment processing between images of step 324 of FIG. 17.

At step 340 of FIG. 18, the montage image generation section 1425 extracts a feature point group 1 to perform the above positional alignment by performing image processing on the UWF upward looking fundus image GU.

Figure 19A:
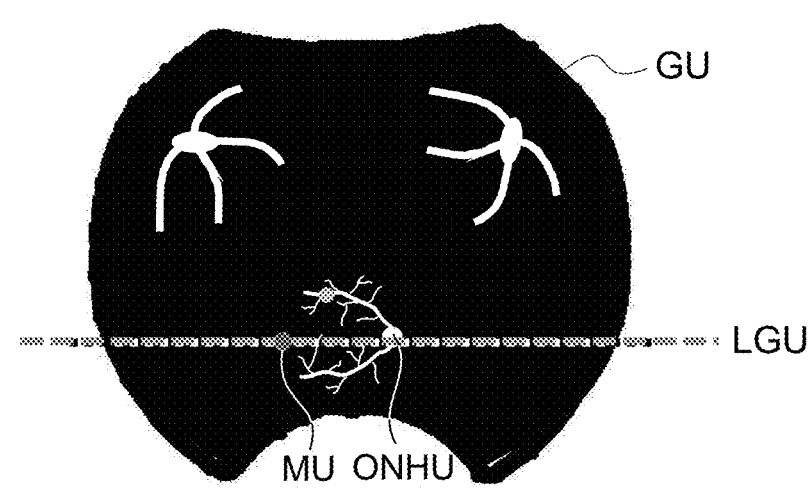
FIG. 19A is a diagram illustrating a manner in which a line segment LGU is set on a UWF upward looking fundus image GU.
Figure 19B:
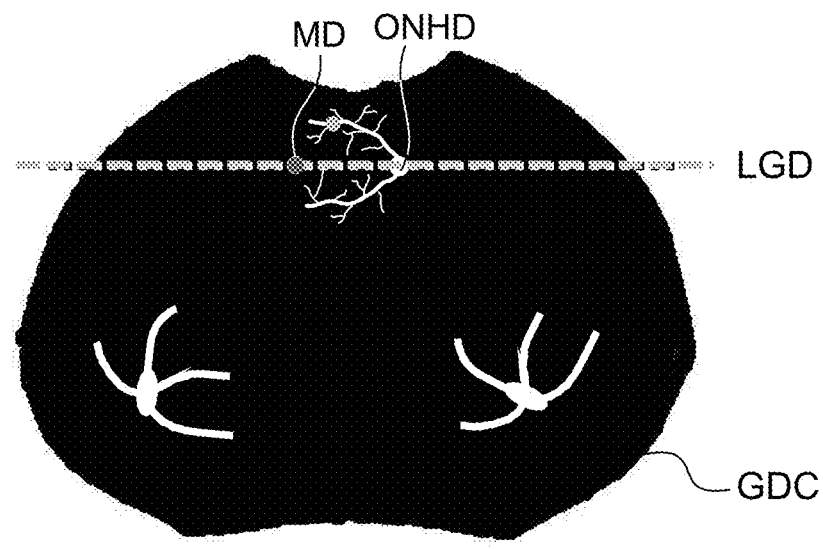
FIG. 19B is a diagram illustrating a manner in which a line segment LGD is set on a UWF downward looking fundus image GDC.
Figure 21:
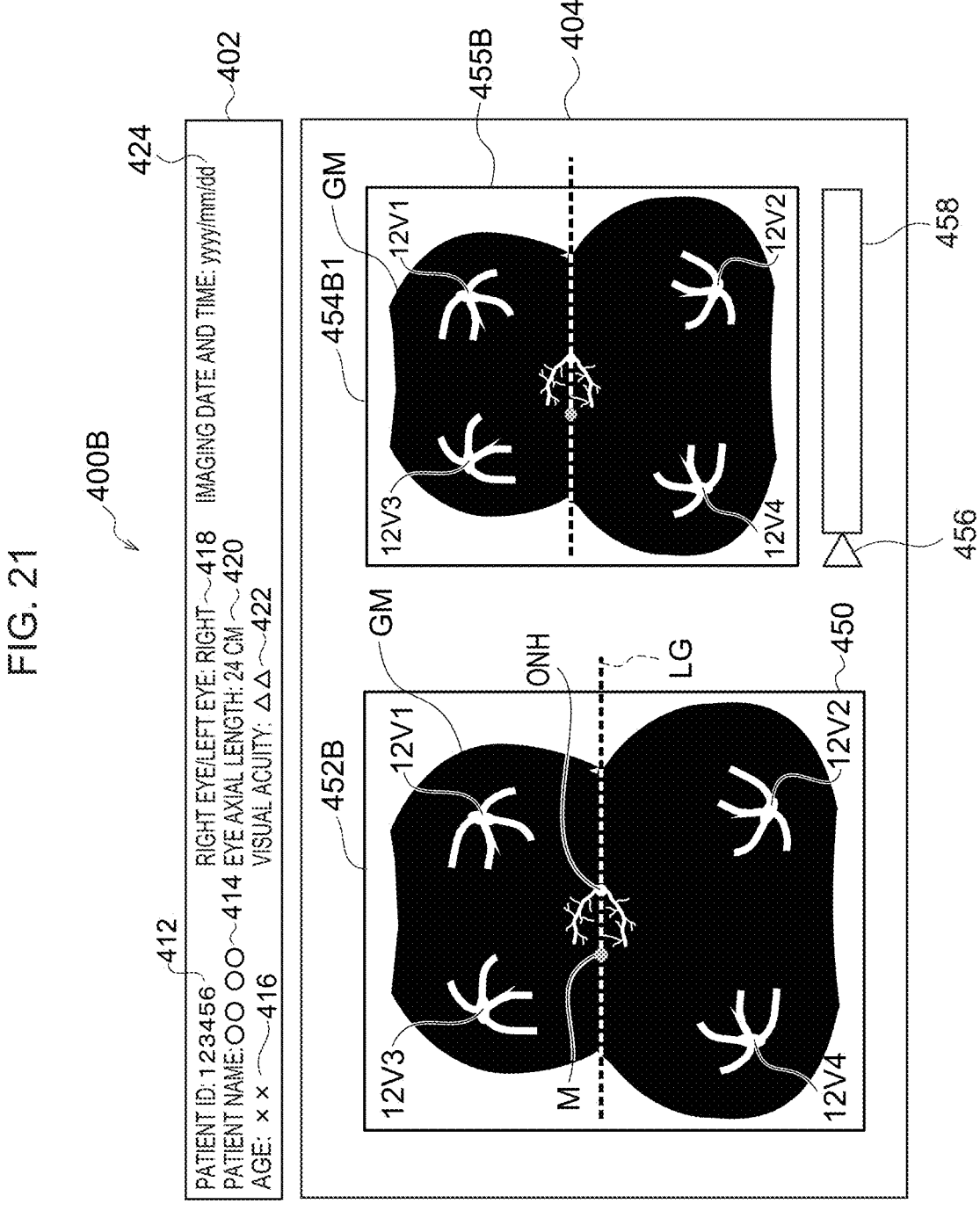
FIG. 21 is a diagram illustrating a first display format of a display screen 400B.

The feature point group 1 is configured by plural feature points on the fundus image, and as illustrated in FIG. 19A includes an optic nerve head ONHU, a macular MU, and branch points of the retinal blood vessels. Note that branch points of the choroidal blood vessels may also be extracted as feature points.

The feature points are pixels of maximum brightness of an optic nerve head ONHU region, pixels of minimum brightness of a macular MU region, pixels at positions of branch points of the retinal blood vessels and the choroidal blood vessels, and the coordinates of these pixels are extracted as feature point data. Alternatively, not only branch points in the retinal blood vessels and the choroidal blood vessels, but regions including a characteristic blood vessel running pattern may be extracted, and center points of the regions including these patterns taken as feature points.

Note that terminal points, curve points, or meander points of the retinal blood vessels and the choroidal blood vessels may be extracted as feature points.

The feature points may use a scale invariant feature transform (SIFT), a speed upped robust feature (SURF), or the like as an algorithm to perform feature point detection.

In order to perform the positional alignment with high accuracy, preferably there is a plural number of four or more of the extracted feature points. There is only one of the optic nerve head and the macular present in the UWF upward looking fundus image GU for the examined eye. Thus four or more of the feature points 1 can be extracted from the UWF upward looking fundus image GU by extracting branch points of the retinal blood vessels or choroidal blood vessels merely at two or more locations.

The optic nerve head, macular, retinal blood vessels, and choroidal blood vessels present at a fundus central portion are preferably selection targets for feature points to use in the positional alignment since they are imaged in both the UWF upward looking fundus image GU and the UWF downward looking fundus image GD. Namely, the feature points are preferably selected from a fundus central portion that is a common region to both the UWF upward looking fundus image GU and the UWF downward looking fundus image GD.

Thus at step 340, the montage image generation section 1425 extracts the feature point group 1 by performing image processing on the fundus central portion that is a region on the lower side of the center of the UWF upward looking fundus image GU.

A vortex vein present at a fundus peripheral portion in the UWF upward looking fundus image GU is excluded from being a target for selection of feature points used in the positional alignment described above. The fundus peripheral portion is not a common region to the UWF upward looking fundus image GU and the UWF downward looking fundus image GD, and so structures in the fundus peripheral portion are excluded from being a target for selection of feature points.

At step 342 the montage image generation section 1425 extracts a feature point group 2 from the UWF downward looking fundus image GD corresponding to the feature point group 1. The feature point group 2 is, as illustrated in FIG. 19B, configured by the optic nerve head ONHD, the macular MD, and branch points in the retinal blood vessels. Due to being in the same eye, the optic nerve head ONHD corresponds to the optic nerve head ONHU, and the macular MD corresponds to the macular MU. The branch points described above in the UWF upward looking fundus image GU correspond to the branch points of the blood vessels in the UWF downward looking fundus image GD. Branch locations having the same branching pattern as the branching pattern of branch points in the UWF upward looking fundus image GU are extracted from the UWF downward looking fundus image GD using image recognition processing or the like.

At step 344 the montage image generation section 1425 employs the feature point group 1 and the feature point group 2 to generate a projection transformation matrix for geometric transformation of the UWF downward looking fundus image GD. The projection transformation matrix is a matrix to transform the UWF downward looking fundus image GD so as to conform to the UWF upward looking fundus image GU. The projection transformation matrix is defined by at least four feature points.

At step 346, the generated projection transformation matrix is employed to transform the UWF downward looking fundus image GD so as to obtain the UWF downward looking fundus image GDC after transformation (see FIG. 19B). The feature point group 1 and the feature point group 2 both arrive at the same position after transformation using the projection transformation matrix, and positional alignment processing has been executed. Due to the transformation, the UWF downward looking fundus image GDC is larger than the UWF downward looking fundus image GD (there is an increase in the surface area).

In the above description the projection transformation matrix is generated to make the UWF downward looking fundus image GD conform to the UWF upward looking fundus image GU, and the UWF downward looking fundus image GD is transformed. On the other hand, a projection transformation matrix may be generated to make the UWF upward looking fundus image GU conform to the UWF downward looking fundus image GD, and the UWF upward looking fundus image GU may be transformed.

The inter-image positional alignment processing is performed thereby, completing step 324 of FIG. 17, and the image processing proceeds to step 326.

At step 326 of FIG. 17, the montage image generation section 1425 combines the UWF upward looking fundus image GU and the UWF downward looking fundus image GDC after transformation to generate a montage image GM.

More specifically, first the montage image generation section 1425 sets a line segment LGU on the UWF upward looking fundus image GU to pass through the optic nerve head ONHU and the macular MU, as illustrated in FIG. 19A. Similarly, the montage image generation section 1425 sets a line segment LGD on the UWF downward looking fundus image GDC after transformation to pass through the optic nerve head ONHD and the macular MD, as illustrated in FIG. 19B.

Figure 20:
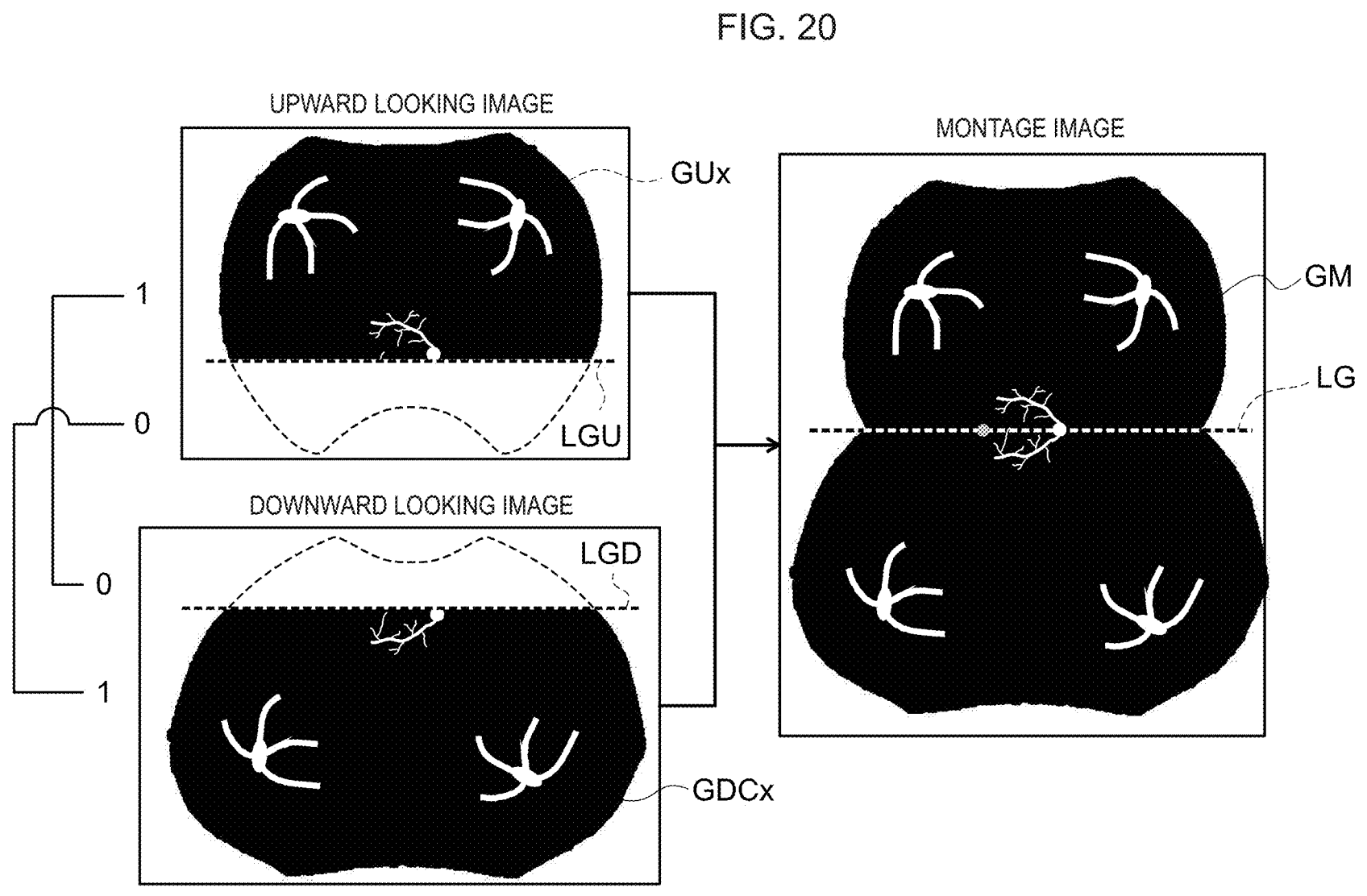

Next, the montage image generation section 1425 performs processing to assign weights to overlapping regions of the UWF upward looking fundus image GU and the UWF downward looking fundus image GDC. As illustrated in FIG. 20, the montage image generation section 1425 assigns a weight of "1" to an upper side UWF upward looking fundus image GUx region that is a region on the upper side of the line segment LGU of the UWF upward looking fundus image GU. The montage image generation section 1425 assigns a weight of "0" to a region on the lower side of the line segment LGU. The montage image generation section 1425 assigns a weight of "1" to a lower side UWF downward looking fundus image GDCx that is a region on the lower side of the line segment LGD of the UWF downward looking fundus image after transformation, and assigns a weight of "0" in a region on the upper side of the line segment LGD.

The montage image generation section 1425 generates a montage image GM combining the UWF upward looking fundus image GUx and the UWF downward looking fundus image GDCx by performing the weighting processing in this manner on the UWF upward looking fundus image GU and the UWF downward looking fundus image GDC. As illustrated in FIG. 20, the line segment LG is a line segment connecting the optic nerve head ONH to the macular M, the upper side of the line segment LG is the UWF upward looking fundus image GUx and the lower side of the line segment LG is the UWF downward looking fundus image GDCx. The montage image is an example of a "montage image" of the technology disclosed herein.

Note that weighting related to the overlapping portions of the UWF upward looking fundus image GU and the UWF downward looking fundus image GDC is not limited the example described above, and various values may be set for a mixing ratio between the UWF upward looking fundus image GU and the UWF downward looking fundus image GDC.

Positional alignment is performed on the UWF upward looking fundus image GU and the UWF downward looking fundus image GDC in this manner and they are combined. The combining enables a fundus image to be obtained to analyze vortex veins positioned in the fundus peripheral portion or the fundus equatorial portion and choroidal blood vessels at the vortex vein periphery without blood vessels of the fundus becoming non-contiguous, or for analyzing abnormal portions, pathological lesions and the like.

Next at step 328 the feature portion acquisition section 1424 uses the montage image GM to analyze the position of the vortex veins and the blood vessel diameter of blood vessels in the vicinity of the vortex veins. Examples of vortex vein information obtained by such analysis include information related to the number of the vortex veins, positions of the vortex veins, the number of blood vessels connected to the vortex veins, and the blood vessel diameter of blood vessels at the periphery of the vortex veins.

After the processing of step 328, the 3D rendering processing is executed at step 504S. At step 504 of the first exemplary embodiment, the image processing section 1420 executes the 3D rendering processing (see also FIG. 6) on the UWF fundus image G1. In contrast thereto, at step 504S in the second exemplary embodiment the image processing section 1420 executes the 3D rendering processing (see also FIG. 6) on the montage image GM. Thus the only difference therebetween is in the image subjected to processing, and so explanation of the 3D rendering processing of step 504S will be omitted.

After step 504S, display screen generation processing is executed at step 506S. Details are given later regarding the display screen of the second exemplary embodiment.

At step 332, the output section 1440 outputs the montage image GM and the vortex vein analysis information obtained by vortex vein analysis to the storage device 254 of the server 140. The montage image GM and the vortex vein analysis information obtained by the vortex vein analysis is stored in the storage device 254 of the server 140.

At step 332, the output section 1440 also outputs image data corresponding to a display screen 400B to the viewer 150.

Note that the display control section 1430 may output an instruction to the display 256 to display the montage image GM.

Next, description follows regarding the display screen 400B of the second exemplary embodiment. The display screen 400B of the second exemplary embodiment is substantially similar to the display screen 400A of the first exemplary embodiment, and so only differing parts will be explained.

The display screen 400B includes an image display area 404B instead of the image display area 404A. The image display area 404B includes a montage image display field 452B and a video data display field 454B1.

The montage image is displayed in the montage image display field 452B.

When the replay button 456 is operated, the video data is displayed on a video data display section 455B, and a bar graph of the proportion already displayed from out of the entire video data is displayed in the display progress display section 458.

The replay of video data on the video data display section 455B is similar to that of the first exemplary embodiment and so explanation thereof will be omitted.

Figure 22:
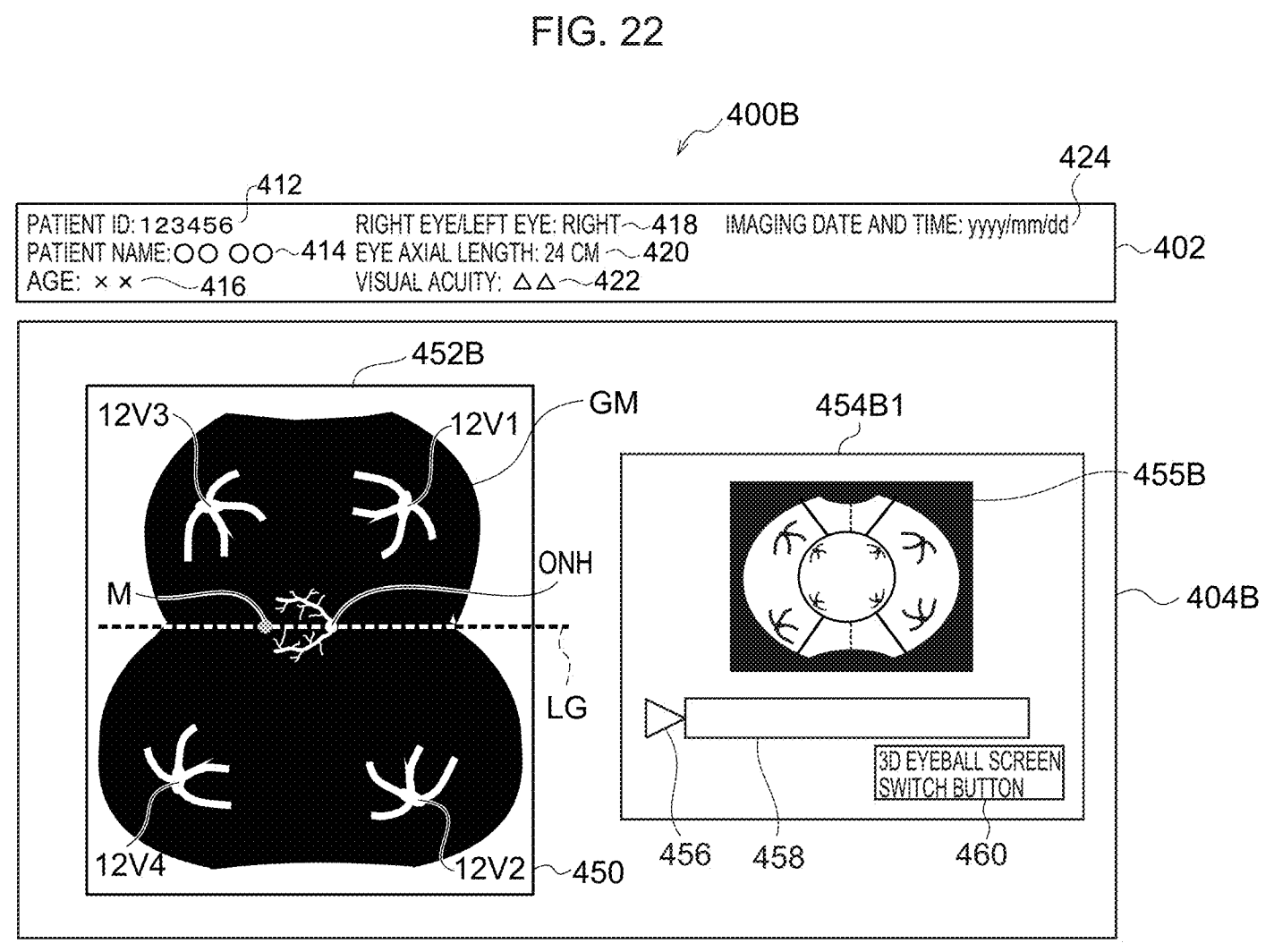
Figure 23:
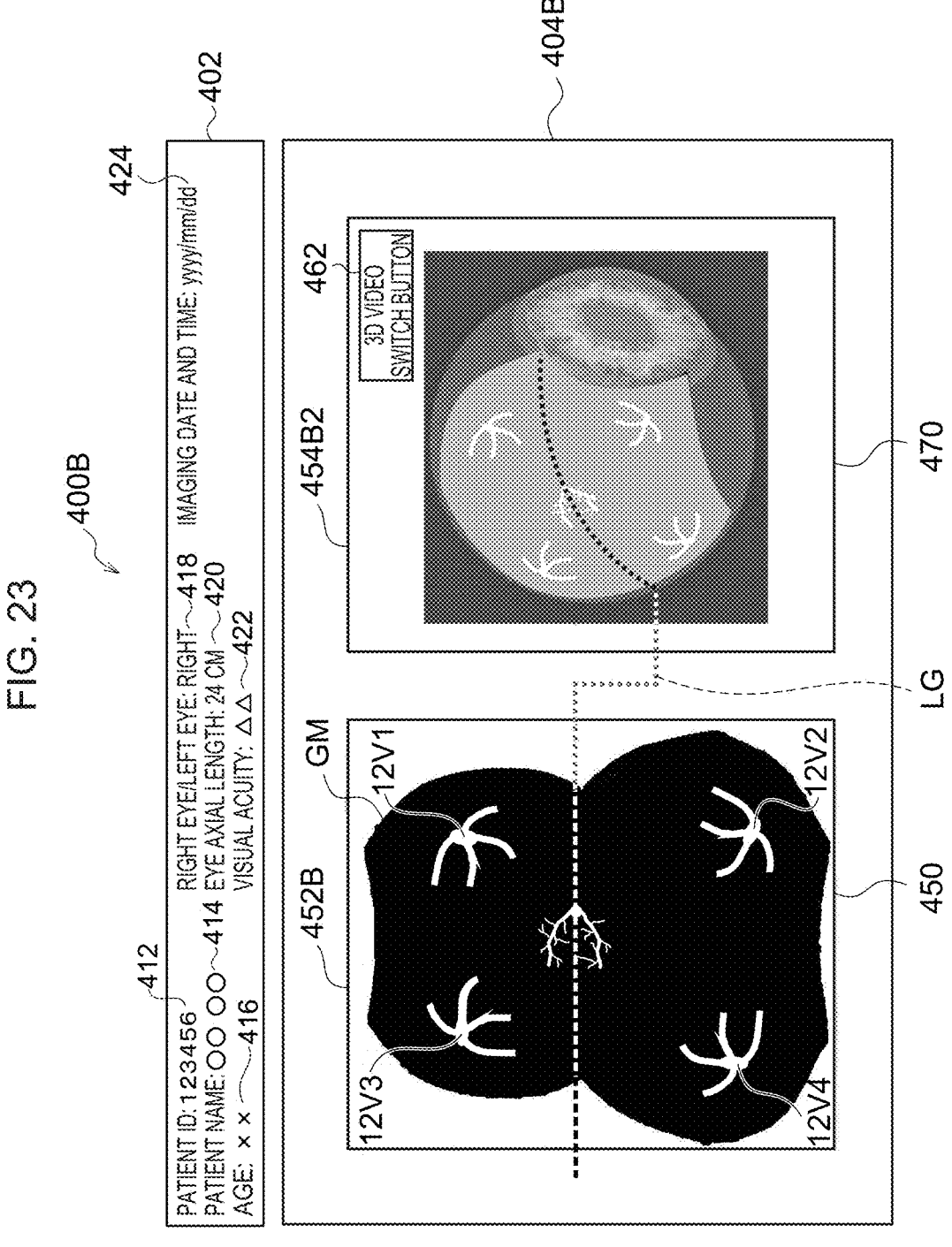
FIG. 23 is a diagram illustrating a third display format of the display screen 400B.

When the video data is displayed on the video data display section 455 and an image Gz (FIG. 13) is displayed, as illustrated in FIG. 22, an 3D eyeball image switch button 460 is displayed in a video data display field 454B1. When the 3D eyeball image switch button 460 is operated, as illustrated in FIG. 23, a switch is made to a 3D fundus image display field 454B2 instead of the video data display field 454B1. A 3D fundus image is displayed in the 3D fundus image display field 454B2. As described above, the 3D fundus image displayed has feature portions emphasized on an image after the pixels of all points on the montage image have been moved to points on the eyeball model M corresponding to these pixel points.

In the second exemplary embodiment as described above, video data is created to represent the process to move each of the points of the montage image to the corresponding point on the eyeball model. Thus the way in which each of the points of the montage image moves to the corresponding point on the eyeball model can be known. This enables which point each of the corresponding points on the eyeball model is on the montage image to be known.

Moreover, the montage image includes a wider area than the UWF fundus image of the first exemplary embodiment, and so which point on the montage image of the wider area than the UWF fundus image is related to each of the corresponding points on the eyeball model can be known. Thus a user is able to directly ascertain a position on the eyeball of vortex veins and pathological changes such as a detached retina simply by the user viewing the video data generated from the montage image. The ophthalmologist is able to explain to the examinee (patient) the results of examination, such as the position and size of pathological change in the fundus peripheral portion, in a manner that is easier to understand.

A method described in International Publication (WO) No. PCT/JP2019/021868 may be employed as the method to acquire the UWF upward looking fundus image and the UWF downward looking fundus image, and the method to create the montage image. The entire disclosure of WO No. PCT/JP2019/021868 filed on May 31, 2019 is incorporated in the present specification by reference herein.

Next explanation follows regarding various modified examples of the technology disclosed herein.

The configuration of each of the modified examples is similar to the configuration of the first exemplary embodiment, and so explanation thereof will be omitted below. The operation of each of the modified examples is substantially similar to the operation of the first exemplary embodiment, and so explanation will mainly be of differing parts. In the first exemplary embodiment video data is created to represent the process to move pixels at each of the points on the UWF fundus image to respective corresponding points on the eyeball model. However, the technology disclosed herein is not limited thereto.

First Modified Example

Figure 24:
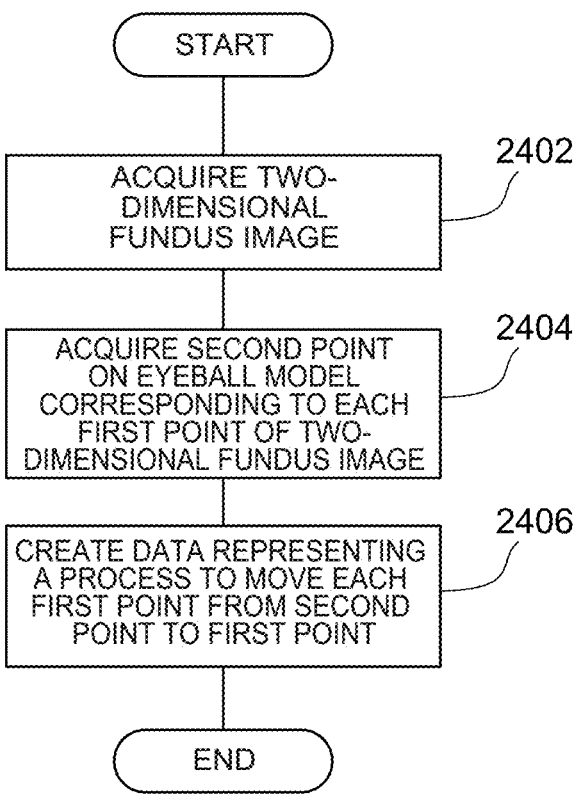
FIG. 24 is a flowchart of image processing by a server 140 of a first modified example.

Explanation follows regarding image processing of a first modified example, with reference to FIG. 24.

At step 2402, the image acquisition section 1410 acquires a two-dimensional fundus image (UWF fundus image G1 or montage image) corresponding to the patient ID from the storage device 254.

At step 2404, the 3D video generation section 1421 acquires each of second points on the eyeball model M, which has been corrected according to eye axial length, corresponding to each of first points of the two-dimensional fundus image.

At step 2406, the 3D video generation section 1421 creates data (video data) representing a process to move each of the first points from a corresponding second point to this first point.

This enables a user to know the way in which of each of the first points of the UWF fundus image moves from a respective corresponding second point on the eyeball model to the first point.

Second Modified Example

Figure 25:
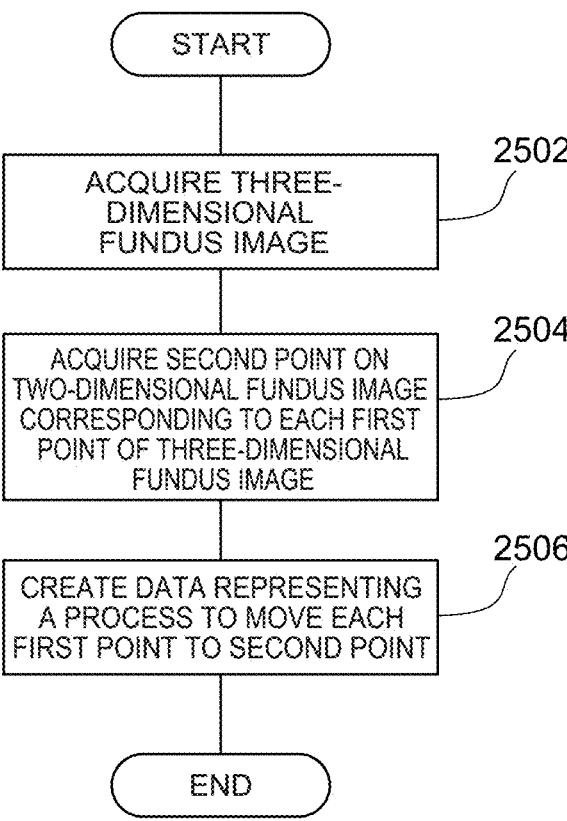
FIG. 25 is a flowchart of image processing by a server 140 of a second modified example.

Explanation follows regarding image processing of the second modified example, with reference to FIG. 25.

In the second modified example, data for a three-dimensional fundus image is generated in advance by reverse stereographic projection of a two-dimensional fundus image (UWF fundus image G1 or montage image) onto an eyeball model corrected according to eye axial length, and the data is stored in the storage device 254 associated with the patient ID.

At step 2502, the image acquisition section 1410 acquires three-dimensional fundus image data corresponding to the patient ID from the storage device 254.

At step 2504, the 3D video generation section 1421 acquires each of the second points on the two-dimensional fundus image corresponding to each of the first points of the three-dimensional fundus image.

At step 2506, the 3D video generation section 1421 creates data (video data) representing a process to move each of the first points to the corresponding second point.

This enables a user to know the way in which each of the first points of the three-dimensional fundus image moves to each of the corresponding second points on the two-dimensional fundus image.

Third Modified Example

Figure 26:
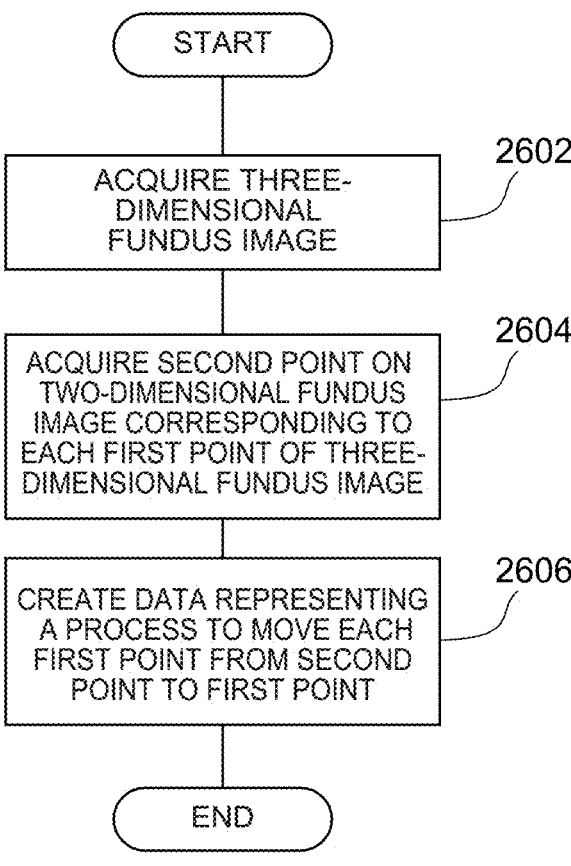
FIG. 26 is a flowchart of image processing by a server 140 of a third modified example.

Explanation follows regarding image processing of a third modified example, with reference to FIG. 26.

In the third modified example, data of a three-dimensional fundus image is generated in advance similarly to in the second modified example, and the data is stored in the storage device 245 associated with the patient ID.

At step 2602, the image acquisition section 1410 acquires data of the three-dimensional fundus image corresponding to the patient ID from the storage device 254.

At step 2604, the 3D video generation section 1421 acquires each of the second points on the two-dimensional fundus image corresponding to each of the first points on the three-dimensional fundus image.

At step 2606, the 3D video generation section 1421 creates data (video data) representing a process to move each of the first points from the corresponding second point to the first point.

This enables a user to know the way in which each of the first points of the three-dimensional fundus image moves from each of the corresponding second points on the two-dimensional fundus image to the first point.

Other Modified Examples

The data of the three-dimensional fundus image in each of the examples described above may be obtained by reverse stereographic projection of a two-dimensional fundus image (UWF fundus image G1 or montage image) onto an eyeball model. However the technology disclosed herein is not limited thereto. For example, OCT volume data, OCT angiograph data, three-dimensional fundus image data obtained by MRI or ultrasound, or three-dimensional image data such as of an anterior eye portion, may be employed.

In the first exemplary embodiment video data is created representing a process to move pixels at all points of a UWF fundus image to corresponding points on an eyeball model. In the second exemplary embodiment video data is created representing a process to move all the pixels of a montage image to corresponding points on the eyeball model. However the technology disclosed herein is not limited thereto.

Video data may be created for the movement described above of a pixel at least at one point selected by a user.

In such cases the user may select plural points in an area by stipulating the area of the UWF fundus image or the montage image.

The user may also stipulate the above-mentioned feature portion of the eyeball as the area. More specifically, the user may stipulate, for example, a lens body, a fundus structure, a pathological lesion, or the like as the feature portion.

In the first exemplary embodiment video data is created to represent a process to move pixels at each point of the UWF fundus image (UWF-SLO fundus image) to each of the corresponding points on the eyeball model. In the second exemplary embodiment video data is created to represent a process to move pixels at each point of the montage image (combined image of the UWF-SLO fundus image) to each of the corresponding points on the eyeball model. However, the technology disclosed herein is not limited thereto.

Video data may be created to represent a process to move pixels at each point of a retinal vascular image or a choroidal vascular image obtained from the UWF-SLO image or the montage image (combined image of the UWF-SLO fundus image) to each of the corresponding points on the eyeball model.

Moreover, instead of a UWF-SLO image, for example, video data may be created to represent a process to move pixels at each point of a fundus image obtained by a fundus camera to each of the corresponding points on the eyeball model.

Video data is created in the first exemplary embodiment and the second exemplary embodiment. However, technology disclosed herein is not limited thereto. For example, at least one image may be created to represent a process to move pixels at each point of a UWF fundus image to each of the corresponding points on the eyeball model. For example, an image may be created of a position where a pixel at a point of the UWF fundus image is positioned at an intermediate position between at least one point of the UWF fundus image and the corresponding point on the eyeball model.

In the respective examples described above, the image processing of FIG. 5 and FIG. 17 is executed by the server 140, however the technology disclosed herein is not limited thereto. For example, this processing may be executed by the ophthalmic device 110 or the viewer 150, or a separate other image processing device may be connected to the network 130 and this processing executed by this image processing device.

Although explanation has been given in the respective examples described above regarding an example in which a computer is employed to implement image processing using a software configuration, the technology disclosed herein is not limited thereto. For example, instead of a software configuration employing a computer, the image processing may be executed solely by a hardware configuration such as a field programmable gate array (FPGA) or an application specific integrated circuit (ASIC). Alternatively, a configuration may be adopted in which some processing out of the image processing is executed by a software configuration, and the remaining processing is executed by a hardware configuration.

Such technology disclosed herein encompasses cases in which the image processing is implemented by a software configuration utilizing a computer, and also cases in which the image processing is implemented by a configuration that is not a software configuration utilizing a computer, and encompasses the following first technology to third technology.

First Technology

An image processing device image including:

an image acquisition section configured to acquire a two-dimensional fundus image;

a point acquisition section configured to acquire a second point on an eyeball model corresponding to at least one first point of the two-dimensional fundus image; and a creation section configured to create data to represent a process to move a pixel at the at least one first point to the second point.

Note that the 3D video generation section 1421 is an example of a "point acquisition section" and a "creation section".

Second Technology

An image processing method including:

an image acquisition section acquiring a two-dimensional fundus image;

a point acquisition section acquiring a second point on an eyeball model corresponding to at least one first point of the two-dimensional fundus image; and a creation section creating data to represent a process to move a pixel at the at least one first point to the second point.

The following third technology is proposed from the content disclosed above.

Third Technology

A computer program product for image processing, the computer program product including a computer-readable storage medium that is not itself a transitory signal, with a program stored on the computer-readable storage medium, the program causing a computer to execute processing including:

acquiring a two-dimensional fundus image;

acquiring a second point on an eyeball model corresponding to at least one first point of the two-dimensional fundus image; and creating data to represent a process to move a pixel at the at least one first point to the second point.

It must be understood that the image processing described above is merely an example thereof. Obviously redundant steps may be omitted, new steps may be added, and the processing sequence may be swapped around within a range not departing from the spirit of the present disclosure.

All publications, patent applications and technical standards mentioned in the present specification are incorporated by reference in the present specification to the same extent as if each individual publication, patent application, or technical standard was specifically and individually indicated to be incorporated by reference.

The invention claimed is:

1. An image processing method in which image processing is performed by a processor, the image processing method comprising:

acquiring a two-dimensional fundus image;

acquiring a second point on an eyeball model corresponding to at least one first point of the two-dimensional fundus image; and creating data to represent a process to move the at least one first point to the second point.

2. The image processing method of claim 1, wherein the data is video data configured from a plurality of frames.

3. The image processing method of claim 2, wherein:

the process is set for each of a specific interval of time;

a frame is generated for each specific interval of time for an intermediate position for moving a pixel at the at least one first point; and the video data includes a frame at the at least one first point, frames at a plurality of intermediate positions set between the at least one first point and the second point, and a frame at the second point.

4. The image processing method of claim 1, wherein:

a plurality of movement patterns are predetermined for the movement; and the data is data representing a process of moving according to a movement pattern selected from among the plurality of movement patterns.

5. The image processing method of claim 4, wherein the movement pattern is a path connecting the at least one first point and the second point in three-dimensional space.

6. The image processing method of claim 5, wherein the path is a straight line path connecting the at least one first point and the second point.

7. The image processing method of claim 4, wherein the movement pattern includes data related to a movement speed for the at least one first point to move to the second point.

8. The image processing method of claim 1, wherein the at least one first point is a point selected from among a plurality of points on the two-dimensional fundus image.

9. The image processing method of claim 1, wherein the at least one first point is respective points in a stipulated area of the two-dimensional fundus image.

10. The image processing method of claim 1, wherein the at least one first point is respective points in the entire two-dimensional fundus image.

11. The image processing method of claim 1 wherein the at least one first point is a point corresponding to a single pixel configuring the two-dimensional fundus image.

12. The image processing method of claim 1, wherein the eyeball model is a model resulting from a default eyeball model being corrected according to an eye axial length.

13. The image processing method of claim 1 wherein the two-dimensional fundus image is a montage image resulting from combining a first direction fundus image imaged in a state in which a gaze of an examined eye is facing in a first direction together with a second direction fundus image imaged in a state in which the examined eye is facing in a second direction different from the first direction.

14. An image processing device comprising:

a memory, and a processor coupled to the memory, wherein the processor is configured to:

acquire a two-dimensional fundus image;

acquire a second point on an eyeball model corresponding to at least one first point of the two-dimensional fundus image; and create data to represent a process to move the at least one first point to the second point.

15. A non-transitory storage medium storing a program to cause a computer to execute processing comprising:

acquiring a two-dimensional fundus image;

acquiring a second point on an eyeball model corresponding to at least one first point of the two-dimensional fundus image; and creating data to represent a process to move the at least one first point to the second point.

\* \* \* \* \*